US012758432B2

(12) United States Patent
Simmons

(10) Patent No.: US 12,758,432 B2
(45) Date of Patent: Oct. 13, 2026

(54) NEGATIVE-PRESSURE THERAPY DRESSING WITH FLUID TRANSPORT FEATURES

(71) Applicant: KCI Manufacturing Unlimited Company, Westmeath (IE)

(72) Inventor: Tyler H. Simmons, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 563 days.

(21) Appl. No.: 18/274,556

(22) PCT Filed: Jan. 20, 2022

(86) PCT No.: PCT/IB2022/050467
§ 371 (c)(1),
(2) Date: Jul. 27, 2023

(87) PCT Pub. No.: WO2022/175762
PCT Pub. Date: Aug. 25, 2022

(65) Prior Publication Data

US 2024/0074912 A1 Mar. 7, 2024

Related U.S. Application Data

(60) Provisional application No. 63/150,974, filed on Feb. 18, 2021.

(51) Int. Cl.
*A61F 13/05* (2024.01)
*A61M 1/00* (2006.01)

(52) U.S. Cl.
CPC ............. *A61F 13/05* (2024.01); *A61M 1/915* (2021.05); *A61M 1/96* (2021.05)

(58) Field of Classification Search
CPC .......... A61F 13/05; A61M 1/915; A61M 1/96
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

PCT International Search Report/Written Opinion for PCT International Application No. PCT/IB2022/050467, mailed Jun. 2, 2022.
(Continued)

*Primary Examiner* — Jessica Arble

(57) ABSTRACT

Disclosed embodiments may relate to dressings configured to provide negative-pressure therapy to a tissue site, such as an incision. In some embodiments, the dressing may comprise a manifold and a cover configured to be disposed over the manifold on a tissue site. Some embodiments of the cover may comprise a plurality of fluid transport features, such as channels, on the interior surface of the cover. In some embodiments, the fluid transport features may be configured for capillary action.

28 Claims, 18 Drawing Sheets

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A * | 8/1995 | Todd .................... A61M 1/915 604/323 |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 6,855,135 | B2 * | 2/2005 | Lockwood .............. A61F 13/05 604/313 |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0318072 | A1 * | 12/2010 | Johnston ................... A47L 9/02 604/543 |
| 2014/0163491 | A1 | 6/2014 | Schuessler et al. |
| 2015/0080788 | A1 | 3/2015 | Blott et al. |
| 2018/0353338 | A1 * | 12/2018 | Locke ................. A61F 13/0223 |

FOREIGN PATENT DOCUMENTS

| | | | |
|---|---|---|---|
| AU | 755496 | B2 | 12/2002 |
| CA | 2005436 | A1 | 6/1990 |
| CN | 107049603 | B | 1/2021 |
| DE | 2640413 | A1 | 3/1978 |
| DE | 4306478 | A1 | 9/1994 |
| DE | 29504378 | U1 | 9/1995 |
| EP | 0100148 | A1 | 2/1984 |
| EP | 117632 | A2 | 9/1984 |
| EP | 161865 | A2 | 11/1985 |
| EP | 358302 | A2 | 3/1990 |
| EP | 1018967 | A1 | 7/2000 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |

(56) References Cited

FOREIGN PATENT DOCUMENTS

| | | | |
|---|---|---|---|
| WO | 94020041 | A1 | 9/1994 |
| WO | 9605873 | A1 | 2/1996 |
| WO | 9718007 | A1 | 5/1997 |
| WO | 9913793 | A1 | 3/1999 |
| WO | 2009124473 | A1 | 10/2009 |
| WO | 2015061352 | A2 | 4/2015 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, The Use of Hypermia in the Postoperative Treatment of Lesions of the Extremities and Thorax, Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

NEGATIVE-PRESSURE THERAPY DRESSING WITH FLUID TRANSPORT FEATURES

CROSS-REFERENCE TO RELATED APPLICATIONS

This application claims the benefit of priority to U.S. Provisional Application No. 63/150,974, filed on Feb. 18, 2021, which is incorporated herein by reference in its entirety.

TECHNICAL FIELD

This disclosure relates generally to tissue treatment systems and more particularly, but without limitation, to dressings, systems, and methods relating to negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for managing tissue sites in a negative-pressure therapy environment are set forth in the appended claims. The following description provides non-limiting, illustrative example embodiments to enable a person skilled in the art to make and use the claimed subject matter.

Disclosed embodiments may relate to negative-pressure dressings for use on a tissue site. Embodiments may have a manifold layer and a cover, with the cover configured to be disposed over the manifold layer. The interior surface of the cover (e.g. facing the manifold) may comprise a plurality of fluid transport features. For example, the fluid transport features may be channels extending longitudinally on the interior surface of the cover. In some embodiments, each of the channels may be formed by a groove located between adjacent ridges. Some embodiments may have channels only on the top cap portion of the cover, while other embodiments may also have channels located on some or all of the sidewalls of the cover. In some embodiments, the ridges may comprise taller ridges and shorter ridges, for example with a plurality of shorter ridges located between adjacent taller ridges.

By way of example, in some example embodiments, a negative-pressure dressing may comprise: a manifold having a first (e.g. tissue-facing) surface and a second surface (e.g. configured to face away from the tissue site); and a cover configured to be disposed over the manifold. In some embodiments, the cover may comprise: an interior surface configured so that at least a portion of the interior surface faces towards the second surface of the manifold, an exterior surface, and a plurality of fluid transport features on at least a portion of the interior surface. In some embodiments, at least a portion of the plurality of fluid transport features may be configured for capillary action. Some embodiments of the cover may further comprise a port configured for introduction of negative pressure through the cover. In some embodiments, the plurality of fluid transport features may comprise a plurality of channels sized for capillary action. In some embodiments, the manifold may be elongate; and the fluid transport features may be oriented to extend longitudinally along an elongate length of the manifold. In some embodiments, the cover may further comprise a plurality of sidewalls and a top cap; and the fluid transport features may be located on the top cap. In some embodiments, the plurality of sidewalls of the cover may comprise two longitudinal sidewalls and two end sidewalls; and the fluid transport features may also be located on the longitudinal sidewalls or on all of the sidewalls. In some embodiments, the plurality of fluid transport features may comprise a plurality of channels; and the plurality of channels may comprise a plurality of ridges and a plurality of grooves. In some embodiments, at least some of the grooves may have a width configured to provide fluid transport via capillary action, even when negative pressure in the dressing is insufficient to induce fluid transport. In some embodiments, the channels may be configured to provide two different mechanisms for fluid movement through the dressing independent of the manifold. For example, the plurality of ridges may comprise a first portion of taller ridges and a second portion of shorter ridges; the taller ridges may have a height greater than the shorter ridges; two or more of the shorter ridges may be located between each pair of adjacent taller ridges; the taller ridges may be configured to form flow channels for transportation of fluid under negative pressure independent of the manifold (e.g. without the need for fluid to flow through the manifold); and the shorter ridges may be configured to transport fluid by capillary action. In some embodiments, the cover may further comprise a hydrophilic coating on the interior surface. Some dressing embodiments may further comprise an attachment device configured to sealingly attach the cover to the tissue site. In some embodiments, the cover may further comprise a flange; and the attachment device may be configured to attach the flange to the tissue site.

In some example embodiments, a negative-pressure dressing may comprise: an attachment device having a treatment aperture; a manifold having a first surface and a second surface and configured for the first surface to be at least partially exposed to the tissue site through the treatment aperture; and a cover configured to be disposed over the manifold and coupled to the attachment device around the manifold. In some embodiments, the cover may comprise: an interior surface configured with a top cap portion facing towards the second surface of the manifold, an exterior surface, and a plurality of exudate transport features on at least a portion of the interior surface. In some embodiments, at least a portion of the plurality of exudate transport features may be configured for capillary action. For example, the plurality of exudate transport features may comprise a plurality of channels sized for capillary action. In some embodiments, the manifold may be elongate; and the exudate transport features may be oriented to extend longitudinally. Some dressing embodiments may further comprise a port configured for introduction of negative pressure through the cover.

In some example embodiments, a negative-pressure dressing may comprise: a fluid-control layer comprising a substantially fluid-impermeable polymer film with a plurality of fluid passages extending through the polymer film; a manifold having a first surface, a second surface, and a thickness therebetween, wherein the first surface is disposed adjacent to the fluid-control layer; and a substantially fluid-impermeable cover configured to be disposed over the manifold (e.g. opposite the fluid-control layer). In some embodiments, the cover may comprise: an interior surface configured with at least a portion of the interior surface facing towards the second surface of the manifold, and a plurality of liquid channeling features on at least a portion of the interior surface. In some embodiments, at least a portion of the plurality of liquid channeling features may be configured for capillary action. For example, the plurality of liquid channeling features may comprise a plurality of channels sized for capillary action; the manifold may be elongate; and the liquid channeling features may be oriented to extend longitudinally. In some embodiments, the cover may further comprise a port configured for introduction of negative pressure through the cover. Some embodiments may further comprise a sealing layer disposed adjacent to the fluid control layer opposite the manifold, the sealing layer having a plurality of apertures at least partially aligned with the fluid passages of the fluid-control layer.

In some example embodiments, a negative-pressure dressing may comprise: a manifold having a first surface (e.g. configured to face towards the tissue site) and a second surface (e.g. configured to face away from the tissue site); and a cover configured to be disposed over the manifold. In some embodiments, the cover may comprise an interior surface configured so that at least a top cap portion of the interior surface faces towards the second surface of the manifold, a port configured for introduction of negative pressure through the cover and/or to the manifold, and a plurality of micro-molded features on at least a portion of the interior surface configured for longitudinal fluid transport along the dressing. In some embodiments, at least a portion of the micro-molded features may be configured for capillary action. In some embodiments, at least a portion of the micro-molded features may be configured for fluid transport due to negative pressure differential within the dressing. In some embodiments, the portion micro-molded features configured for capillary action may comprise a plurality of shorter ridges separated by a plurality of grooves. In some embodiments, the portion of the micro-molded features configured for fluid transport due to negative pressure differential may comprise taller ridges, and two or more shorter ridges may be located between adjacent taller ridges.

In some example embodiments, a drape or cover for a negative-pressure dressing may comprise a polymer film having: an interior surface configured so that at least a portion of the interior surface faces towards and/or contacts a manifold, and a plurality of fluid transport features on at least a portion of the interior surface. In some embodiments, at least some of the plurality of fluid transport features may be configured for capillary action. Some embodiments of the drape may further comprise a port configured for introduction of negative pressure through the drape, for example to the manifold. Some dressing embodiments may comprise the drape, along with a manifold underlying the drape.

In some example embodiments, a method for manufacturing a dressing may comprise: providing a manifold; and providing a cover having an interior surface, configured so that at least a portion of the interior surface faces towards the manifold, and a plurality of fluid transport features on at least a portion of the interior surface. In some embodiments, at least some of the plurality of fluid transport features may be configured for capillary action. For example, the plurality of fluid transport features may comprise a plurality of channels sized for capillary action. In some embodiments, the manifold may be elongate, and the plurality of channels may extend longitudinally. Some method embodiments may further comprise attaching the cover to a surface of the manifold. Some embodiments may further comprise providing an attachment device having a treatment aperture, and positioning the manifold so that at least a portion of the manifold (e.g. opposite the cover) is exposed to, faces, and/or is in fluid communication with the tissue site through the treatment aperture. Some embodiments may further comprise attaching the cover to the attachment device. In some embodiments, the cover may comprise a top cap and a plurality of sidewalls. In some embodiments, the fluid transport features may be located on the top cap and/or the sidewalls. For example, the method may comprise forming a cover with a top cap and a plurality of sidewalls. In some embodiments, forming the cover may further comprise forming the top cap to have at least some of the plurality of fluid transport features and/or forming the sidewalls to have at least some of the fluid transport features. Some embodiments may further comprise providing a fluid control layer, a comfort or protection layer, and/or a sealing layer. Some embodiments may further comprise positioning the fluid control layer and/or the comfort layer between the manifold and the tissue site, for example between the manifold and the treatment aperture of the attachment device. In some embodiments, providing a cover may comprise providing a polymer film, for example comprising polyurethane or polyethylene, and forming the fluid transport features on the interior surface. Some embodiments may further comprise orienting the cover with respect to the elongate manifold so that the fluid transport features extend longitudinally. Some embodiments may further comprise forming a port in the cover, configured for introduction of negative pressure into the dressing.

In some example embodiments, a method of using a dressing may comprise: applying a negative-pressure dressing (similar to disclosed embodiments) to a tissue site, applying negative pressure to the dressing, and transporting fluid (e.g. longitudinally and/or towards a port) within the dressing via capillary action. For example, the dressing may comprise a plurality of channels (e.g. ridges and grooves) which are configured for capillary action. In some embodiments, the manifold may not effectively transport fluid under negative pressure (e.g. the manifold may be clogged), and the capillary action fluid transport may allow fluid movement despite ineffective distribution of negative pressure throughout the dressing. Some method embodiments may further comprise orienting the dressing vertically, wherein transporting fluid via capillary action may transport fluid vertically even when the negative pressure within the dressing is insufficient to effectively transport fluid vertically.

Objectives, advantages, and a preferred mode of making and using the claimed subject matter may be understood best by reference to the accompanying drawings in conjunction with the following detailed description of illustrative example embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and non-limiting.

Figure 1:
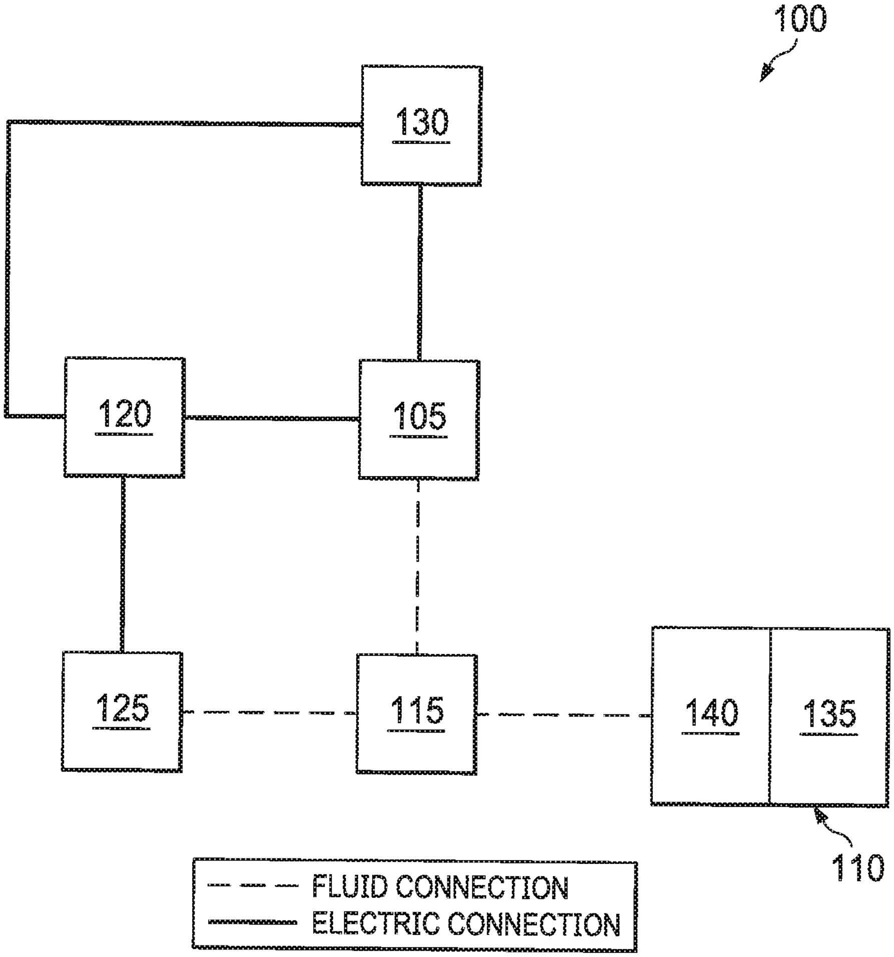
FIG. 1 is a block diagram of an example embodiment of a therapy system that can provide negative-pressure therapy in accordance with this specification.

FIG. 1 is a block diagram of an example embodiment of a therapy system 100 that can provide negative-pressure therapy to a tissue site in accordance with this specification. The term "tissue site" in this context may refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, and incisions, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of reduced or negative pressure, such as a negative-pressure source 105, a dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include one or more sensors coupled to the controller 120, such as a first sensor 125 and a second sensor 130. As illustrated in the example of FIG. 1, the dressing 110 may include a tissue interface 135, a cover 140, or both in some embodiments. The dressing 110 may also be referred to as a dressing assembly in some examples, which may include additional or different features as described herein.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 120 and other components into a therapy unit.

In general, components of the therapy system 100 may be coupled directly or indirectly. For example, the negative-pressure source 105 may be directly coupled to the container 115, and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component may be detachable, and may be disposable, reusable, or recyclable. The dressing 110 and the container 115 are illustrative of distribution components. A fluid conductor is another illustrative example of a distribution component. A "fluid conductor," in this context, may include a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad available from KCI of San Antonio, Texas.

A negative-pressure supply, such as the negative-pressure source 105, may be a reservoir of air at a reduced pressure, or may be a manual or electrically-powered device, such as a vacuum pump, a suction pump, a wall suction port available at many healthcare facilities, or a micro-pump, for example. "Negative pressure" or "reduced pressure" generally refers to a pressure less than a local ambient pressure, such as the ambient pressure in a local environment external to a sealed therapeutic environment. In many cases, the local ambient pressure may also be the atmospheric pressure at which a tissue site is located. Further, the pressure may be less than a hydrostatic pressure associated with tissue at the tissue site. Unless otherwise indicated, values of pressure stated herein are gauge pressures. References to increases in reduced pressure may refer to a decrease in absolute pressure, while decreases in reduced pressure may refer to an increase in absolute pressure. While the amount and nature of reduced pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 120, may be a microprocessor or computer programmed to operate one or more components of the therapy system 100, such as the negative-pressure source 105. In some embodiments, for example, the controller 120 may be a microcontroller, which may include an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 135, for example. The controller 120 may also be configured to receive one or more input signals, such as a feedback signal, and programmed to modify one or more operating parameters based on the input signals.

Sensors, such as the first sensor 125 and the second sensor 130, may be any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezoresistive strain gauge. The second sensor 130 may optionally measure operating parameters of the negative-pressure source 105, such as the voltage or current, in some embodiments. Signals from the first sensor 125 and the second sensor 130 may be suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

The tissue interface 135 can be adapted to partially or fully contact a tissue site. The tissue interface 135 may take many forms, and may have many sizes, shapes, or thicknesses depending on a variety of factors, such as the type of treatment being implemented or the nature and size of a tissue site. For example, the size and shape of the tissue interface 135 may be adapted to the contours of deep and irregular shaped tissue sites. Moreover, any or all of the surfaces of the tissue interface 135 may have projections or an uneven, course, or jagged profile that can induce strains and stresses on a tissue site, which can promote granulation at the tissue site.

In some embodiments, the tissue interface 135 may be a manifold or may include a manifold and additional layers, components, or features, such as a tissue contact layer, depending on the desired treatment. A "manifold" in this context may include any substance or structure providing a plurality of pathways adapted to collect or distribute fluid relative to a tissue. For example, a manifold may be adapted to receive reduced pressure from a source and distribute reduced pressure through multiple apertures to or from a tissue site, which may have the effect of collecting fluid from a tissue site and drawing the fluid toward the source. In some embodiments, the fluid path may be reversed or a secondary fluid path may be provided to facilitate delivering or moving fluid relative to a tissue site.

In some illustrative embodiments, the pathways of a manifold may be interconnected to improve distribution or collection of fluids at a tissue site. In some illustrative embodiments, a manifold may be a porous foam material having interconnected cells or pores. For example, open-cell foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively include projections that form interconnected fluid pathways. For example, a manifold may be molded to provide surface projections that define interconnected fluid pathways.

In some embodiments, the manifold may comprise or consist essentially of a reticulated and/or open-cell foam having pore sizes and free volume that may vary according to needs of a prescribed therapy. For example, a reticulated foam having a free volume of at least 90% may be suitable for many therapy applications, and/or a foam having an average pore size in a range of 400-600 microns (e.g. 40-50 pores per inch) may be particularly suitable for some types of therapy. The tensile strength of the manifold may also vary according to needs of a prescribed therapy. For example, the tensile strength of a foam may be increased for instillation of topical treatment solutions. The 25% compression load deflection of the manifold may be at least 0.35 pounds per square inch, and the 65% compression load deflection may be at least 0.43 pounds per square inch. In some embodiments, the tensile strength of the manifold may be at least 10 pounds per square inch. The manifold may have a tear strength of at least 2.5 pounds per inch. In some embodiments, the manifold may be a foam comprised of polyols such as polyester or polyether, isocyanate such as toluene diisocyanate, and polymerization modifiers such as amines and tin compounds. In some examples, the manifold may be a reticulated polyurethane foam such as used in GRANUFOAM™ dressing or V.A.C. VERAFLO™ dressing, both available from KCI of San Antonio, Texas.

In some embodiments, the manifold may comprise an open-cell foam having a free volume in a range of about 18% to about 45%, a density of about 2.6-8.0 lb/ft3, about 80-250 pores per inch on average (e.g., as measured in the direction of compression), and/or average pore size of about 80-300 micron (e.g., as measured in the direction of compression). In some embodiments, the density of the foam of the manifold may be about 3.9-4.8 lb/ft3. In some embodiments, the free volume of the foam may be in a range of about 18% to about 30%. In some embodiments, the free volume of the foam may be about 30%. In some embodiments, the average pore size of the foam may be about 133-200 micron. In some embodiments, the foam of the manifold may have 120-150 pores per inch on average. For example, the manifold may comprise or consist essentially of a foam having 120-135 pores per inch on average. In some embodiments, the foam of the manifold may have a 25% compression load deflection of at least 1.05 pounds per square inch and a 65% compression load deflection of at least 1.29 pounds per square inch. In some embodiments, the foam of the manifold may have a 25% compression load deflection of about 1.05-1.75 pounds per square inch and a 65% compression load deflection of about 1.29-2.15 pounds per square inch.

In some embodiments, the manifold may be formed by a felting process. Any porous foam suitable for felting may be used, including the example foams mentioned herein, such as found in GRANUFOAM™ dressing. In general, felting comprises a thermoforming process that permanently compresses a foam to increase the density of the foam while maintaining interconnected pathways. For example, in order to create felted foam, such as felted polyurethane, a foam blank of uncompressed material can be heated to an optimum forming temperature and then compressed. The felting process may alter certain properties of the original material, including pore shape and/or size, elasticity, density, and density distribution. For example, struts that define pores in the foam may be deformed during the felting process, resulting in flattened pore shapes. The deformed struts can also decrease the elasticity of the foam. The density of the foam is generally increased by felting. In some embodiments, contact with hot-press platens in the felting process can also result in a density gradient in which the density is greater at the surface and the pores size is smaller at the surface.

A felted foam may be characterized by a firmness factor, which is indicative of the compression of the foam. The firmness factor of a felted foam can be specified as the ratio of original thickness to final thickness. A compressed or felted foam may have a firmness factor greater than 1. The degree of compression may affect the physical properties of the felted foam. For example, felted foam has an increased effective density compared to a foam of the same material that is not felted. The felting process can also affect fluid-to-foam interactions. For example, as the density increases, compressibility or collapse may decrease. Therefore, foams which have different compressibility or collapse may have different firmness factors. In some example embodiments, a manifold firmness factor (e.g. for the manifold) can range from about 2 to about 5, preferably about 3 to about 5. For example, the firmness factor of the manifold felted foam may be about 3 in some embodiments. There is a general linear relationship between firmness level, density, pore size (or pores per inch) and compressibility. For example, foam found in a GRANUFOAM™ dressing that is felted to a firmness factor of 3 will show a three-fold density increase and compress to about a third of its original thickness.

In some embodiments, a suitable foam blank (e.g. of pre-felted foam) for formation of the manifold may have 40-50 pores per inch on average, a density of 1.3-1.6 lb/ft3, a free volume of about 90% or more, an average pore size in a range of 400-600 micron, a 25% compression load deflection of at least 0.35 pounds per square inch, and/or a 65% compression load deflection of at least 0.43 pounds per square inch. In some embodiments, the foam blank may have a thickness greater than 10 mm, for example 10-35 mm, 10-25 mm, 10-20 mm, 15-20 mm, 16-24 mm, 16-40 mm, 24-40 mm, 20-30 mm, 20-50 mm, or 30-50 mm. In other embodiments, the foam blank may have a thickness from 8-10 mm, and the felting process may result in a thinner manifold. In some embodiments, the foam blank may be felted to provide denser foam for the manifold. For example, the foam blank may be felted to a firmness factor of 2-5. In some embodiments, the foam blank may be felted to a firmness factor of 3-5. Some embodiments may felt the foam blank to a firmness factor of 3.

The tissue interface 135 may be either hydrophobic or hydrophilic. In an example in which the tissue interface 135 may be hydrophilic, the tissue interface 135 may also wick fluid away from a tissue site, while continuing to distribute negative pressure to the tissue site. The wicking properties of the tissue interface 135 may draw fluid away from a tissue site by capillary flow or other wicking mechanisms. An example of hydrophilic foam is a polyvinyl alcohol, open-cell foam such as V.A.C. WHITEFOAM™ dressing available from KCI of San Antonio, Texas. Other hydrophilic foams may include those made from polyether. Other foams that may exhibit hydrophilic characteristics include hydrophobic foams that have been treated or coated to provide hydrophilicity.

The tissue interface 135 may further promote granulation at a tissue site when pressure within the sealed therapeutic environment is reduced. For example, any or all of the surfaces of the tissue interface 135 may have an uneven, coarse, or jagged profile that can induce microstrain and stress at a tissue site if negative pressure is applied through the tissue interface 135.

In some embodiments, the tissue interface 135 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 135 may further serve as a scaffold for new cell-growth, or a scaffold material may be used in conjunction with the tissue interface 135 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Some embodiments of the tissue interface 135 may comprise layers, components, or features in addition to the manifold. For example, the tissue interface 135 of an absorptive dressing may comprise an absorbent layer, which may be characterized as exhibiting absorbency and/or as being adapted to absorb liquid (such as exudate) from the tissue site. In some embodiments, the absorbent layer may also be adapted to transfer negative pressure therethrough. In some embodiments, the absorbent layer may be configured to retain exudate and/or other fluids drawn from the tissue site during negative-pressure therapy, which may negate the necessity for separate fluid storage components such as an external fluid container. The absorbent layer may comprise any material capable of absorbing liquid (e.g. any absorbent material). In some embodiments, the absorbent layer may exhibit absorbency of at least 3 g saline/g, or at least 5 g saline/g, or from 8 to 20 g saline/g. In some embodiments, the absorbent layer may comprise superabsorbent material, such as superabsorbent polymer (SAP) particles or fibers. For example, some embodiments of the absorbent layer may comprise or consist essentially of one of the following: polyacrylate, sodium polyacrylate, polyacrylamide copolymer, ethylene-maleic anhydride copolymer, polyvinyl alcohol copolymer, cross-linked hydrophilic polymers, and combinations thereof. In some embodiments, the absorbent layer may be hydrophilic. In an example in which the absorbent layer is hydrophilic, the absorbent layer may also absorb or wick fluid away from one or more other components or layers of the dressing 110. In such an embodiment, the wicking properties of the absorbent layer may draw fluid away from one or more components or layers of the dressing 110 by capillary flow or other wicking mechanisms. An example of hydrophilic foam is a polyvinyl alcohol, open-cell foam. Other hydrophilic foams may include those made from polyether. Other foams that may exhibit hydrophilic characteristics include hydrophobic foams that have been treated or coated to provide hydrophilicity.

In some embodiments, the absorbent layer may have a bag-like structure for holding superabsorbent material. For example, the absorbent layer may be configured with superabsorbent material within a wicking pouch. In some embodiments, the pouch may comprise a first wicking layer and a second wicking layer. In some embodiments, the first wicking layer and the second wicking layer may be coupled around the pouch perimeter to form the enclosed pouch encapsulating (e.g. securely holding) the superabsorbent material to contain and prevent the superabsorbent material from migrating out of the pouch. For example, the first and second wicking layers may be coupled to each other using adhesive. The wicking layers may each comprise wicking material. The wicking material may be configured to be permeable to liquid (such as exudate), while retaining the superabsorbent material within the pouch. For example, the porosity of the wicking layers may be sufficiently small to prevent migration of the superabsorbent material through the wicking layers. The wicking layers may be configured to wick liquid along the superabsorbent material in a lateral direction normal to a thickness of the superabsorbent material within the pouch. Wicking of liquid laterally may enhance the distribution of liquid to the superabsorbent material, which may in turn speed absorption and/or allow for the superabsorbent material to maximize its absorbency. Examples of the wicking material may comprise or consist essentially of one of the following: Viscose, PET, Lidro™ non-woven material, a knitted polyester woven textile material, such as the one sold under the name InterDry® AG material from Coloplast A/S of Denmark, GORTEX® material, DuPont Softesse® material, etc., and combinations thereof. In some embodiments, the absorbent layer may serve as the manifold. For example, the absorbent layer may have manifolding properties, such that a separate manifold may not be necessary for negative-pressure therapy.

Some embodiments of the tissue interface 135 may comprise a protective layer (e.g. a tissue-contact layer). In some embodiments, the protective layer may act as a comfort layer, configured to improve comfort at the tissue site. For example, the comfort layer may comprise a wicking layer or a porous fabric. In some embodiments, the protective layer may act as a fluid control layer, configured to minimize maceration, backflow of exudate out of the dressing to the tissue site, and/or tissue in-growth from the tissue site into the dressing 110. The protective layer may be configured to allow fluid transport from the tissue site into the dressing 110 and/or to manifold during negative-pressure therapy. In some embodiments, the protective layer may be configured as the tissue-contact surface for the dressing, so that in use it may be located adjacent to and/or in direct contact with the tissue site. In some embodiments, the protective layer may be located between the tissue-contact surface and the manifold and/or the absorbent layer. In some embodiments, the protective layer may be located between the tissue site (when the dressing is in use) and the manifold and/or absorbent layer.

In some embodiments, the protective layer may comprise a porous fabric, a porous film, or a polymeric film (e.g. which may be liquid impermeable) with a plurality of fluid passages (e.g. perforations, slits, slots, or fluid valves). In some embodiments, the protective layer (e.g. the comfort layer) may comprise or consist essentially of a woven, elastic material or a polyester knit textile substrate. As a non-limiting example, an InterDry™ textile material from Milliken Chemical of Spartanburg, South Carolina, may be used. The protective layer may also include anti-microbial substances, such as silver, in some embodiments.

In some embodiments, the protective layer may comprise or consist essentially of a liquid-impermeable, elastomeric material. For example, the protective layer may comprise or consist essentially of a polymer film. In some embodiments, for example, the protective layer may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. In some embodiments, the protective layer may be hydrophobic. In some embodiments, the protective layer may be hydrophilic. In some embodiments, the protective layer may be suitable for coupling, such as welding, to other layers, such as the manifold.

Some embodiments of the protective layer may have one or more fluid passages, which can be distributed uniformly or randomly across the protective layer. The fluid passages may be bi-directional and pressure-responsive. For example, each of the fluid passages generally may comprise or consist essentially of an elastic passage that is normally unstrained to substantially reduce liquid flow, and can expand or open in response to a pressure gradient. In some embodiments, the fluid passage may comprise or consist essentially of perforations in the protective layer. Perforations may be formed by removing material from the protective layer. For example, perforations may be formed by cutting through the protective layer, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid passages may be an elastomeric valve that is normally closed when unstrained to substantially prevent liquid flow, and can open in response to a pressure gradient. A fenestration may be a suitable valve for some applications. Fenestrations may also be formed by removing material from the protective layer, but the amount of material removed and the resulting dimensions of the fenestrations may be up to an order of magnitude less than perforations, and may not deform the edges.

For example, some embodiments of the fluid passages may comprise or consist essentially of one or more slits, slots or combinations of slits and slots in the protective layer. In some examples, the fluid passages may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

In some embodiments, the cover 140 may provide a bacterial barrier and protection from physical trauma. The cover 140 may also be constructed from a material that can reduce evaporative losses and provide a fluid seal between two components or two environments, such as between a therapeutic environment and a local external environment. For example, the cover 140 may comprise or consist essentially of an elastomeric film or membrane that can provide a seal adequate to maintain a reduced pressure at a tissue site for a given negative-pressure source. In some example embodiments, the cover 140 may be a polymer drape, such as a polyurethane film, that is permeable to water vapor but impermeable to liquid. The cover 140 may have a high moisture-vapor transmission rate (MVTR) in some applications. For example, the MVTR may be at least 250 g/m^2 per twenty-four hours in some embodiments (based on ASTM E96/E96M for upright cup measurement, e.g. at 38 degrees Celsius and 10% relative humidity). In some embodiments, an MVTR up to 2600 grams per square meter per twenty-four hours or up to 5,000 grams per square meter per twenty-four hours may provide effective breathability and mechanical properties. Such drapes typically have a thickness in the range of 25-50 microns. For permeable materials, the permeability generally should be low enough that a desired negative pressure may be maintained. In some embodiments, the cover 140 may form an outer surface of the dressing 110.

The cover 140 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; an INSPIRE 2301 and INSPIRE 2327 material from Coveris Advanced Coatings of Wrexham, United Kingdom having, for example, an MVTR (inverted cup technique) of 14400 g/m2/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); EVA film; co-polyester; a silicone drape; a 3M Tegaderm® drape; a polyurethane (PU) drape such as one available from Avery Dennison Corporation of Glendale, California; polyether block polyamide copolymer (PEBAX), for example, from Arkema, France; INSPIRE 2327; or other appropriate material.

An attachment device may be used to attach the cover 140 to an attachment surface, such as undamaged epidermis, a gasket, or another cover (e.g. at the tissue site). The attachment device may take many forms. For example, an attachment device may be a medically-acceptable, pressure-sensitive adhesive configured to bond the cover 140 to epidermis around a tissue site. In some embodiments, for example, some or all of the cover 140 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Figure 2:
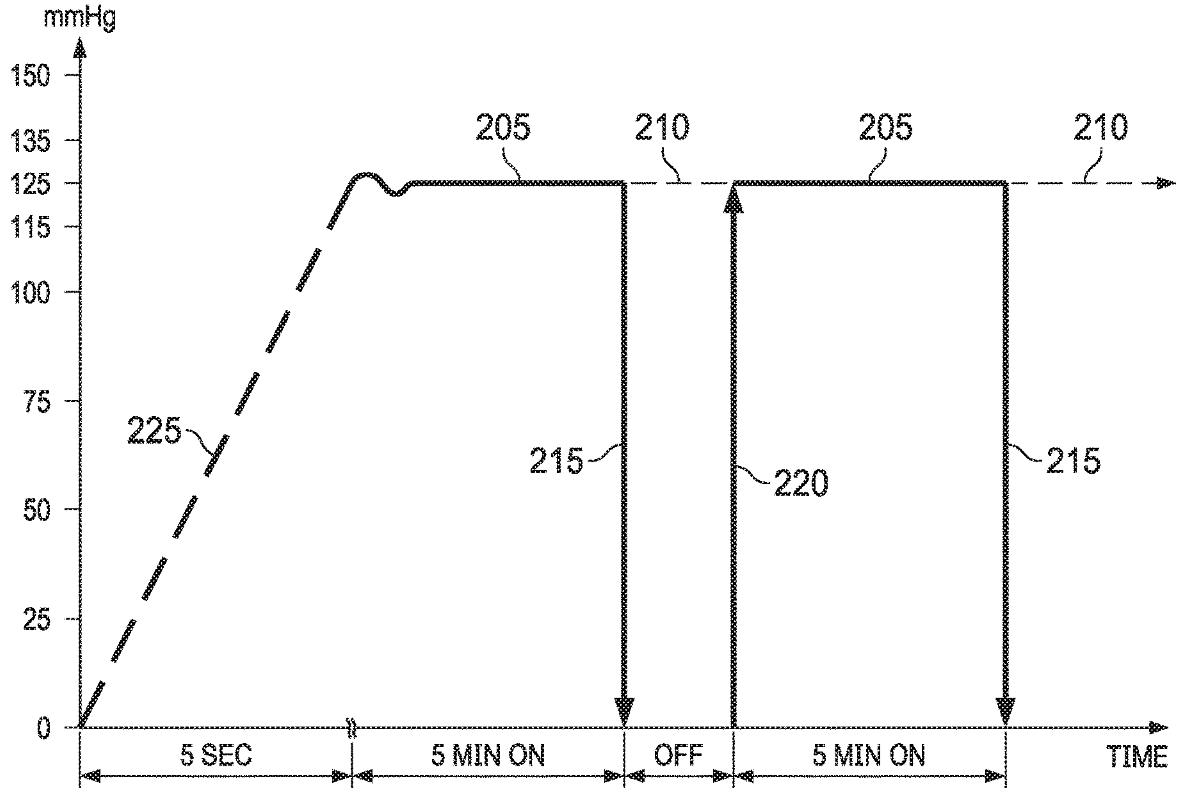
FIG. 2 is a graph illustrating example pressure control modes that may be associated with some example embodiments of the therapy system of FIG. 1.

FIG. 2 is a graph illustrating additional details of an example control mode that may be associated with some embodiments of the controller 120. In some embodiments, the controller 120 may have a continuous pressure mode, in which the negative-pressure source 105 is operated to provide a constant target reduced pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time, and the y-axis represents reduced pressure generated by the negative-pressure source 105 over time. In the example of FIG. 2, the controller 120 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time as indicated by the solid line 220 may be a value substantially equal to the initial rise time as indicated by the dashed line 225.

Figure 3:
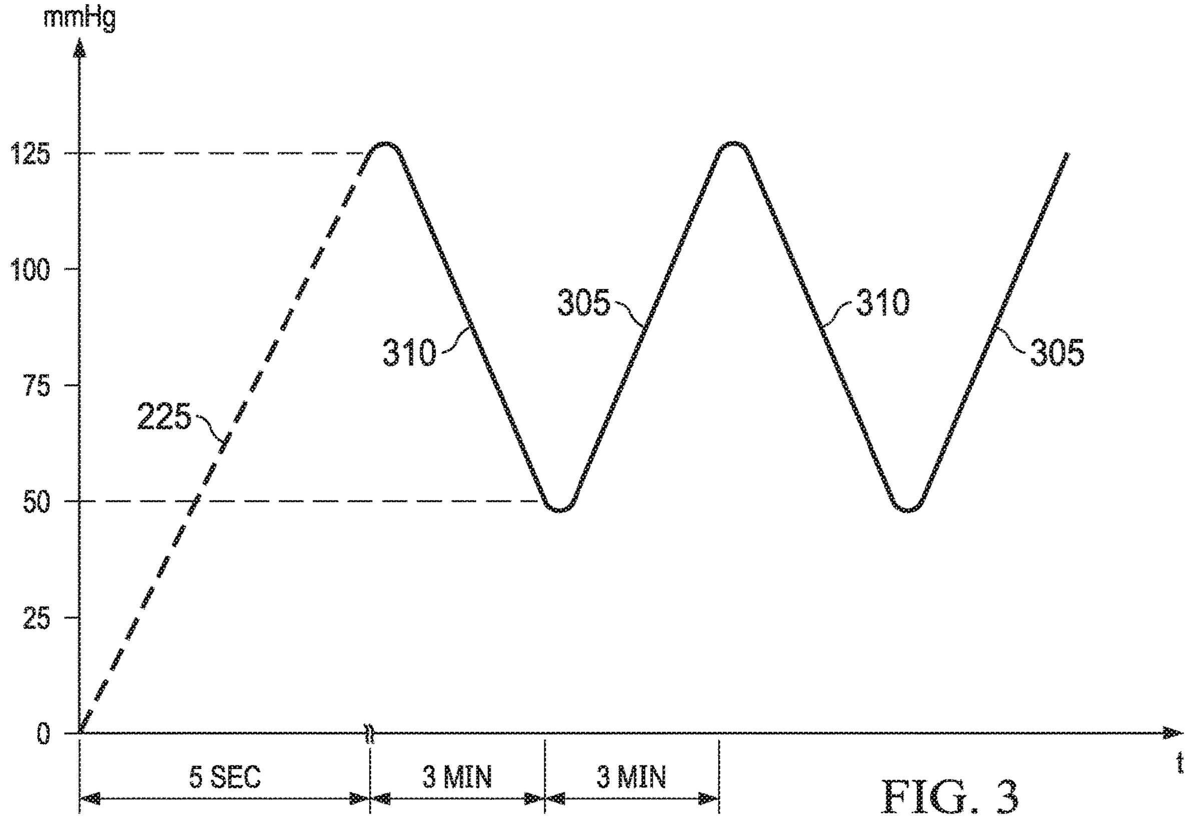
FIG. 3 is a graph illustrating another example pressure control mode suitable for some example embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a minimum and maximum reduced pressure of 50-125 mmHg with a rise time 305 set at a rate of +25 mmHg/min. and a descent time 310 set at −25 mmHg/min, respectively. In other embodiments of the therapy system 100, the triangular waveform may vary between reduced pressure of 25-125 mmHg with a rise time 305 set at a rate of +30 mmHg/min and a descent time 310 set at −30 mmHg/min.

In some embodiments, the controller 120 may control or determine a variable target pressure in a dynamic pressure mode, and the variable target pressure may vary between a maximum and minimum pressure value that may be set as an input prescribed by an operator as the range of desired reduced pressure. The variable target pressure may also be processed and controlled by the controller 120, which can vary the target pressure according to a predetermined waveform, such as a triangular waveform, a sine waveform, or a saw-tooth waveform. In some embodiments, the waveform may be set by an operator as the predetermined or time-varying reduced pressure desired for therapy.

Figure 4:
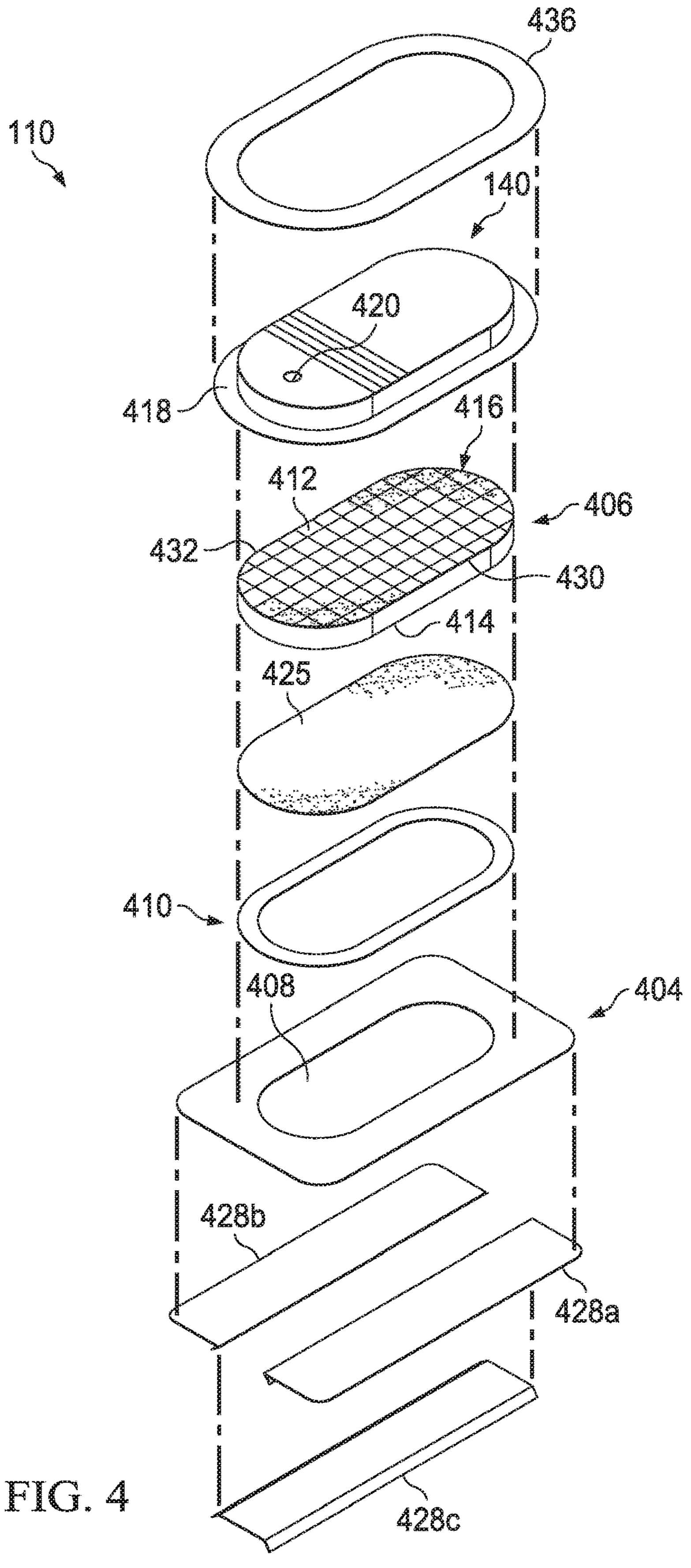
FIG. 4 is an exploded, isometric view of an example embodiment of a dressing that may be associated with an example embodiment of the therapy system of FIG. 1.
Figure 5:
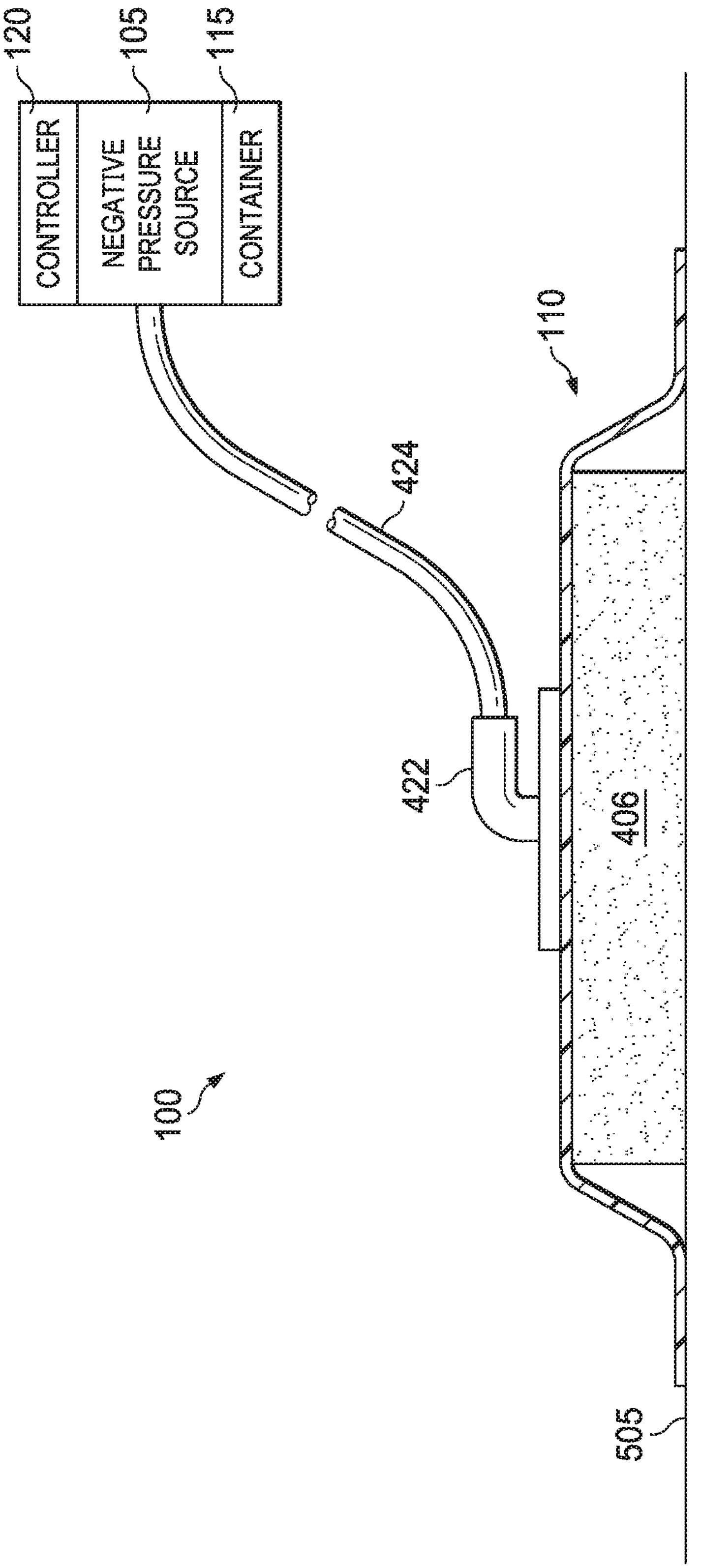
FIG. 5 is a schematic cross-section view illustrating an exemplary system having an exemplary dressing in place on an exemplary tissue site, illustrating additional details that may be associated with some embodiments.

Referring to FIGS. 4-5, the dressing 110 may include features that can treat a tissue site, or parts thereof, and an area of tissue around the tissue/treatment site. For example, the tissue site may be an incision or other treatment target on a patient. The dressing 110 may be configured to treat not only the incision or treatment target, but also, an area of tissue around the incision or treatment target. While the figures may illustrate exemplary dressing embodiments with a particular longitudinal shape, other exemplary dressings may have other sizes, shapes, and/or configurations, for example for use on other tissue sites.

FIG. 4 is an exploded, isometric view of an example embodiment of a dressing or dressing assemblage that may be associated with an example embodiment of the therapy system of FIG. 1. Referring more specifically to FIG. 4, in some examples, the dressing 110 may include an attachment device 404, a manifold 406, and the cover 140. Some examples of the attachment device 404 and other components may include a treatment aperture 408, and the manifold 406 may be configured to be at least partially exposed to a tissue site through the treatment aperture 408. Further, in some examples, the dressing 110 may optionally include an adhesive ring 410 that may be configured to bond a peripheral portion of the manifold 406 to a portion of the attachment device 404. In some examples, the adhesive ring 410 may be formed as part of the attachment device 404, or the adhesive ring 410 may be omitted with the attachment device 404 instead being coupled to the manifold 406 and/or cover 140 with another medically acceptable coupling apparatus. In some examples, the cover 140, the manifold 406, the optional adhesive ring 410, and the attachment device 404 may have similar shapes. The attachment device 404 may be slightly larger than the manifold 406 to permit coupling of the attachment device 404 to the cover 140 around the manifold 406. In some examples, an adhesive may be disposed on a portion of the manifold 406 exposed through the treatment aperture 408. In some embodiments, the adhesive may be pattern-coated, and may cover up to 50% of the exposed portion or surface of the manifold 406.

The cover 140, the manifold 406, the attachment device 404, or various combinations may be assembled, for example forming a pre-assembled dressing assemblage, before application to or at a tissue site. In some embodiments, the dressing 110 (or dressing assemblage) may be provided as a single unit.

The manifold 406 may include a first surface 414 and an opposing second surface 412. In some examples, at least a portion of the first surface 414 (e.g. the tissue-facing surface) of the manifold 406 may be configured to face the tissue site (e.g. the area of tissue around the extremity) through the treatment aperture 408. In some examples, the attachment device 404 may be positioned on or at a portion of the first surface 414 of the manifold 406. In some examples, the manifold 406 may include or be formed of a porous material, such as foam.

In some examples, the attachment device 404 may be configured to create a sealed space between the cover 140 and the tissue site, and the manifold 406 may be configured to be positioned in the sealed space. For example, the attachment device 404 may be positioned around an edge 416 of the manifold 406 and configured to surround the tissue site. The cover 140 may be disposed over the manifold 406 and coupled to the attachment device 404 around the manifold 406. For example, the cover 140 may be coupled to a portion of the attachment device 404 extending outward from the edge 416 of the manifold 406. Further, the cover 140 may be larger than the manifold 406, as illustrated in the example of FIG. 4, and may have a perimeter or a flange 418 configured to be attached to the attachment device 404. Assembled, the cover 140 may be disposed over the second surface 412 (e.g. the outward-facing surface) of the manifold 406, and the flange 418 may be attached to the attachment device 404 around the manifold 406. For example, an adhesive may be used to adhere the flange 418 to the attachment device 404, or the flange 418 may be, without limitation, welded, stitched, or stapled to the attachment device 404. In some embodiments, the attachment device 404 may comprise an adhesive applied to the flange 418 and configured to allow attachment of the flange 418 to the tissue site and/or to a drape on the tissue site. The cover 140 may also include a port 420 configured to allow fluid communication between the manifold 404 and a dressing interface 422 and/or a fluid conductor 424 (e.g. to apply negative pressure under the cover) as described herein.

The attachment device 404 may take many forms. In some examples, the attachment device 404 may include or be formed of a film or membrane that can provide a seal in a therapeutic negative-pressure environment. In some example embodiments, the attachment device 404 may be a polymer film, such as a polyurethane film, that is permeable to water vapor but impermeable to liquid. The attachment device 404 may have a thickness in the range of 25-50 microns. For permeable materials, the permeability may be low enough that a desired reduced pressure may be maintained. The attachment device 404 may also include a medically-acceptable adhesive, such as a pressure-sensitive adhesive. In examples, the attachment device 404 may be a polymer film coated with an adhesive, such as an acrylic adhesive, which may have a coating weight between 25-65 grams per square meter (g.s.m.). Thicker adhesives, or combinations of adhesives, may be applied in some examples to improve the seal and reduce leaks.

In some examples, the attachment device 404 may include or be formed of a hydrocolloid. In some examples, the attachment device 404 may be configured or referred to as a sealing ring or a gasket member. In other examples, the dressing 110 may include a gasket member (not shown) in addition to the attachment device 404. In such an example, the gasket member may be a peripheral member, such as a hydrocolloid ring, and at least a portion of the attachment device 404 may be positioned between the manifold 406 and the gasket member on or at a surface of the manifold 406, such as the first surface 414, configured to face the area of tissue around the tissue site. In some examples, the gasket member may have a similar or analogous shape as the adhesive ring 410, but the gasket member may be positioned on a surface of the attachment device 404 configured to face the tissue site such that the gasket member is configured to be positioned between the tissue site and the attachment device 404.

In some examples, the dressing 110 may optionally further include a protective layer 425, which may be coupled to a surface of the manifold 406, such as the first surface 414, and may be configured to be exposed to the tissue site. In some embodiments, the protective layer 425 may be configured to be positioned in direct contact with the tissue site, for example forming a tissue-contact surface. In other embodiments (e.g. without a protective layer), the tissue-contact surface may be formed by the manifold and/or the attachment device. The protective layer 425 may include or be formed of a material that substantially reduces or eliminates skin irritation while allowing fluid transfer through the protective layer. In some embodiments, the protective layer 425 may form a fluid control layer, configured to allow fluid communication between the tissue site and the manifold during negative-pressure therapy, while minimizing backflow of fluids (such as exudate) from the manifold to the tissue site (e.g. to minimize maceration). In some examples, the protective layer 425 may include or be formed of one or more of the following materials, without limitation: a woven material, a non-woven material, a polyester knit material, and a fenestrated film.

In some examples, the attachment device 404, which may comprise an adhesive on a surface of the dressing 110 configured to face the tissue site (e.g. on the tissue-contact surface), may be covered by one or more release liners 428 prior to applying the dressing 110 at the tissue site. For example, as shown in FIG. 4, the dressing 110 may include a first release liner **428*a*, a second release liner 428*b*, and a third release liner 428*c*. The first release liner 428*a* may be positioned proximate to a first side 430 of the manifold 406 or the dressing 110, the second release liner 428*b* may be positioned proximate to a second side 432 of the manifold 406 or the dressing 110 (e.g. with the first side 430 and the second side 432 opposite each other across a line of symmetry), and the third release liner 428*c* may be positioned proximate to a fold axis, centerline, or line or symmetry of the manifold 406 or the dressing 110 (e.g. spanning a central portion of the manifold and/or dressing). The central portion with the line of symmetry may be located between the first side 430 and the second side 432, and the third release liner 428*c* may be positioned between the first release liner 428*a* and the second release liner 428*b*. In some examples, the third release liner 428*c* may be configured to be removed to expose an adhesive or portion of the attachment device 404 proximate to the line of symmetry prior to removal of the first release liner 428*a* and the second release liner 428*b*. Such a configuration may permit the central portion of the dressing 110 (e.g. in proximity to the line of symmetry) to be initially positioned or aligned at a tissue site, such as the extremity, while the first release liner 428*a* and the second release liner 428*b* protect other portions of the adhesive or the attachment device 404. For example, a portion of the third release liner 428*c* may cover or be positioned over a portion of the first release liner 428*a* and/or the second release liner 428*b* such that the third release liner 428*c* may be removed prior to removal of the first release liner 428*a* and the second release liner 428*b*. In some examples, the dressing 110 may have two release liners, each of which may have perforations or slits (not shown here) configured to allow the release liners to be separated into smaller pieces for removal. Additionally, some embodiments may also have one or more casting sheet liners 436**.

Additionally or alternatively, the first release liner **428*a*, the second release liner 428*b*, and the third release liner 428*c* may provide stiffness to the attachment device 404 to facilitate handling and application. Additionally or alternatively, the casting sheet liners 436 may cover the flange 418 to provide stiffness to the cover 140 for handling and application. The one or more release liner 428 may be configured to releasably cover the attachment device 404, for example to protect and maintain the adhesive of the attachment device 404 until the time of application of the dressing 110** to the tissue site.

FIG. 5 is a schematic view illustrating an exemplary system 100 including a simplified example of the dressing 110 in place on an exemplary tissue site 505, illustrating additional details that may be associated with some embodiments. The system 100 may comprise a negative-pressure source 105 in fluid communication with the dressing 110. For example, the dressing 110 may comprise a dressing interface 422, which may penetrate or fluidly couple with the dressing 110 through the port 420 in the cover 140 to fluidly couple to the manifold 406 of the dressing 110. In some embodiments, a fluid conductor 424 may fluidly couple the negative-pressure source 105 to the dressing interface 422 (thereby fluidly coupling the negative-pressure source 105 to the manifold 406 of the dressing 110, for application of negative-pressure therapy to the tissue site 505 through the manifold 406 of the dressing 110).

In operation, the negative-pressure source 105 can reduce pressure in the sealed therapeutic environment (e.g. when the dressing 110 is applied to the tissue site 505 in the usage configuration). Reduced pressure applied to the tissue site 505 through the manifold 406 in the sealed therapeutic environment can induce macro-strain and/or micro-strain in the tissue site, as well as remove exudates and other fluids from the tissue site 505, which can be collected in the container 115.

In general, exudates and other fluids flow toward lower pressure along a fluid path. Thus, the term "downstream" may refer to a location in a fluid path relatively closer to a source of reduced pressure or further away from a source of positive pressure. Conversely, the term "upstream" may refer to a location further away from a source of reduced pressure or closer to a source of positive pressure.

In some example embodiments, the controller 120 may receive and process data from one or more sensors, such as the first sensor 125. The controller 120 may also control the operation of one or more components of the therapy system 100 to manage the pressure delivered to the tissue interface 135, such as the manifold 406 and associated components. In some embodiments, the controller 120 may include an input for receiving a desired target pressure, and may be programmed for processing data relating to the setting and inputting of the target pressure to be applied to the tissue interface 135. In some example embodiments, the target pressure may be a fixed pressure value set by an operator as the target reduced pressure desired for therapy at a tissue site and then provided as input to the controller 120. The target pressure may vary from tissue site to tissue site based on the type of tissue forming a tissue site, the type of injury or wound (if any), the medical condition of the patient, and the preference of the attending physician. After selecting a desired target pressure, the controller 120 can operate the negative-pressure source 105 in one or more control modes based on the target pressure, and may receive feedback from one or more sensors to maintain the target pressure at the tissue interface 135. In some embodiments, the manifold 406 may have distinct pressure zones, and different target pressures and control modes may be applied to different pressure zones.

Figure 6:
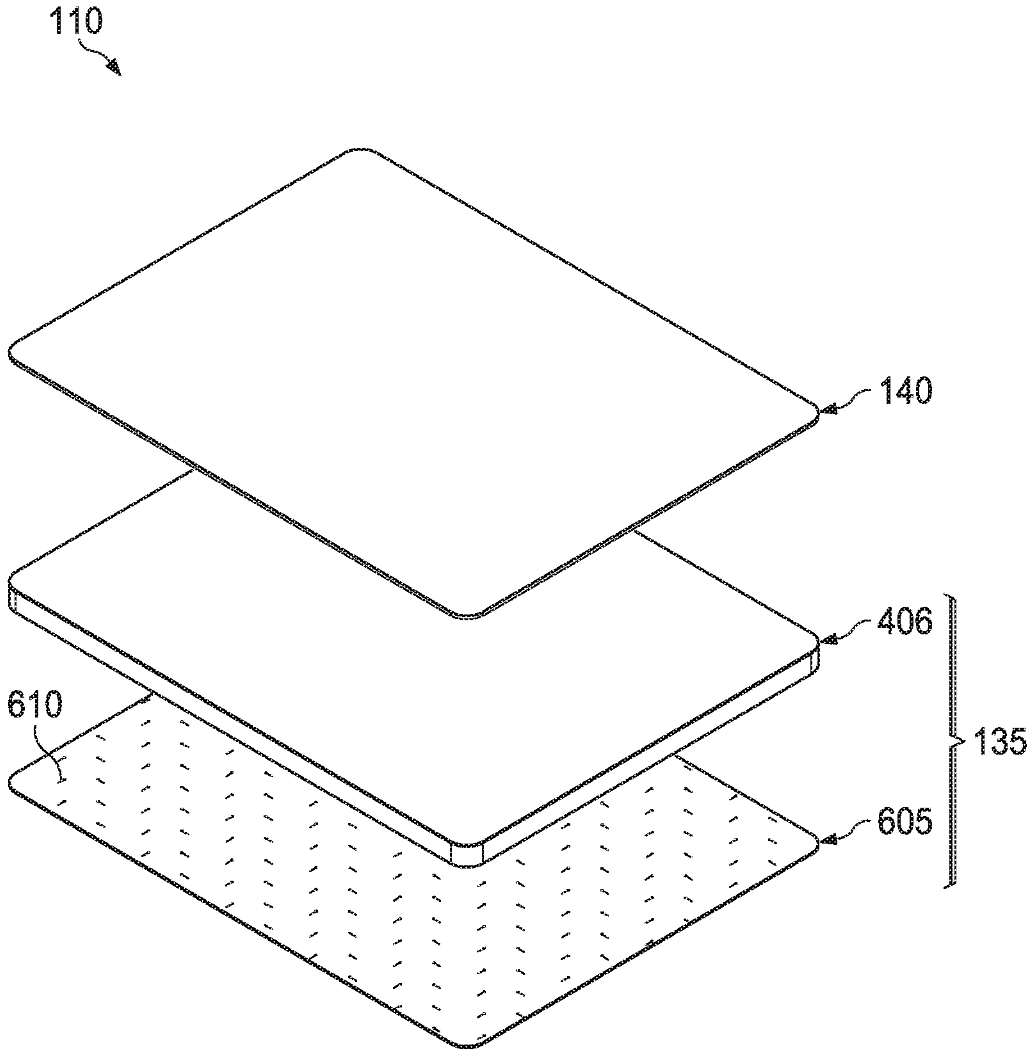
FIG. 6 is an exploded view of another example of a dressing that can be associated with some embodiments of the therapy system of FIG. 1.

FIG. 6 is an assembly view of another example of the dressing 110 of FIG. 1, illustrating additional details that may be associated with some embodiments in which the tissue interface 135 comprises more than one layer. In the example of FIG. 6, the tissue interface 135 comprises a fluid-control layer 605 and a manifold 406. In some embodiments, the fluid-control layer 605 may be disposed adjacent to the manifold 406. For example, the fluid-control layer 605 and the manifold 406 may be stacked so that the fluid-control layer 605 is in contact with the manifold 406. The fluid-control layer 605 may also be heat-bonded or adhered to the manifold 406 in some embodiments. In some embodiments, the fluid-control layer 605 optionally includes a low-tack adhesive, which can be configured to hold the tissue interface 135 in place while the cover 140 is applied. The low-tack adhesive may be continuously coated on the fluid-control layer 605 or applied in a pattern.

The fluid-control layer 605 may comprise or consist essentially of a means for controlling or managing fluid flow. In some embodiments, the fluid-control layer 605 may be a fluid control layer comprising or consisting essentially of a liquid-impermeable, elastomeric material. For example, the fluid-control layer 605 may comprise or consist essentially of a polymer film, such as a polyurethane film. In some embodiments, the fluid-control layer 605 may comprise or consist essentially of the same material as the cover 140. The fluid-control layer 605 may also have a smooth or matte surface texture in some embodiments. A glossy or shiny finish finer or equal to a grade B3 according to the SPI (Society of the Plastics Industry) standards may be particularly advantageous for some applications. In some embodiments, variations in surface height may be limited to acceptable tolerances. For example, the surface of the fluid-control layer 605 may have a substantially flat surface, with height variations limited to 0.2 millimeters over a centimeter.

In some embodiments, the fluid-control layer 605 may be hydrophobic. The hydrophobicity of the fluid-control layer 605 may vary, but may have a contact angle with water of at least ninety degrees in some embodiments. In some embodiments the fluid-control layer 605 may have a contact angle with water of no more than 150 degrees. For example, in some embodiments, the contact angle of the fluid-control layer 605 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the fluid-control layer 605 may be further enhanced with a hydrophobic coating of other materials, such as silicones and fluorocarbons, either as coated from a liquid, or plasma coated.

The fluid-control layer 605 may also be suitable for welding to other layers, including the manifold 406. For example, the fluid-control layer 605 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the fluid-control layer 605 may vary according to a prescribed therapy or application. In some embodiments, an area density of less than 40 grams per square meter may be suitable, and an area density of about 20-30 grams per square meter may be particularly advantageous for some applications.

In some embodiments, for example, the fluid-control layer 605 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

The fluid-control layer 605 may have one or more fluid passages, which can be distributed uniformly or randomly across the fluid-control layer 605. The fluid passages may be bi-directional and pressure-responsive. For example, each of the fluid passages generally may comprise or consist essentially of an elastic passage that is normally unstrained to substantially reduce liquid flow, and can expand or open in response to a pressure gradient. As illustrated in the example of FIG. 6, the fluid passages may comprise or consist essentially of perforations 610 in the fluid-control layer 605. Perforations 610 may be formed by removing material from the fluid-control layer 605. For example, perforations 610 may be formed by cutting through the fluid-control layer 605. In the absence of a pressure gradient across the perforations 610, the perforations 610 may be sufficiently small to form a seal or fluid restriction, which can substantially reduce or prevent liquid flow. Additionally, or alternatively, one or more of the fluid passages may be or may function as an elastomeric valve that is normally closed when unstrained to substantially prevent liquid flow, and can open in response to a pressure gradient. In some examples, the fluid passages may comprise or consist essentially of fenestrations in the fluid-control layer 605. Generally, fenestrations are a species of perforation, and may also be formed by removing material from the fluid-control layer 605. The amount of material removed and the resulting dimensions of the fenestrations may be up to an order of magnitude less than other perforations.

In some embodiments, the perforations 610 may be formed as slots (or fenestrations formed as slits) in the fluid-control layer 605. In some examples, the perforations 610 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect elastomeric valves that can substantially reduce liquid flow in a normally closed or resting state. For example, such slots may form a flow restriction without being completely closed or sealed. The slots can expand or open wider in response to a pressure gradient to allow increased liquid flow.

The manifold 406 generally comprises or consists essentially of a manifold layer, which can provide a means for collecting or distributing fluid across the tissue interface 135 under pressure. In some embodiments, the manifold 406 may comprise or consist essentially of a reticulated and/or open-cell foam having pore sizes and free volume that may vary according to needs of a prescribed therapy. For example, the manifold 406 may comprise a reticulated polyurethane foam.

Figure 7:
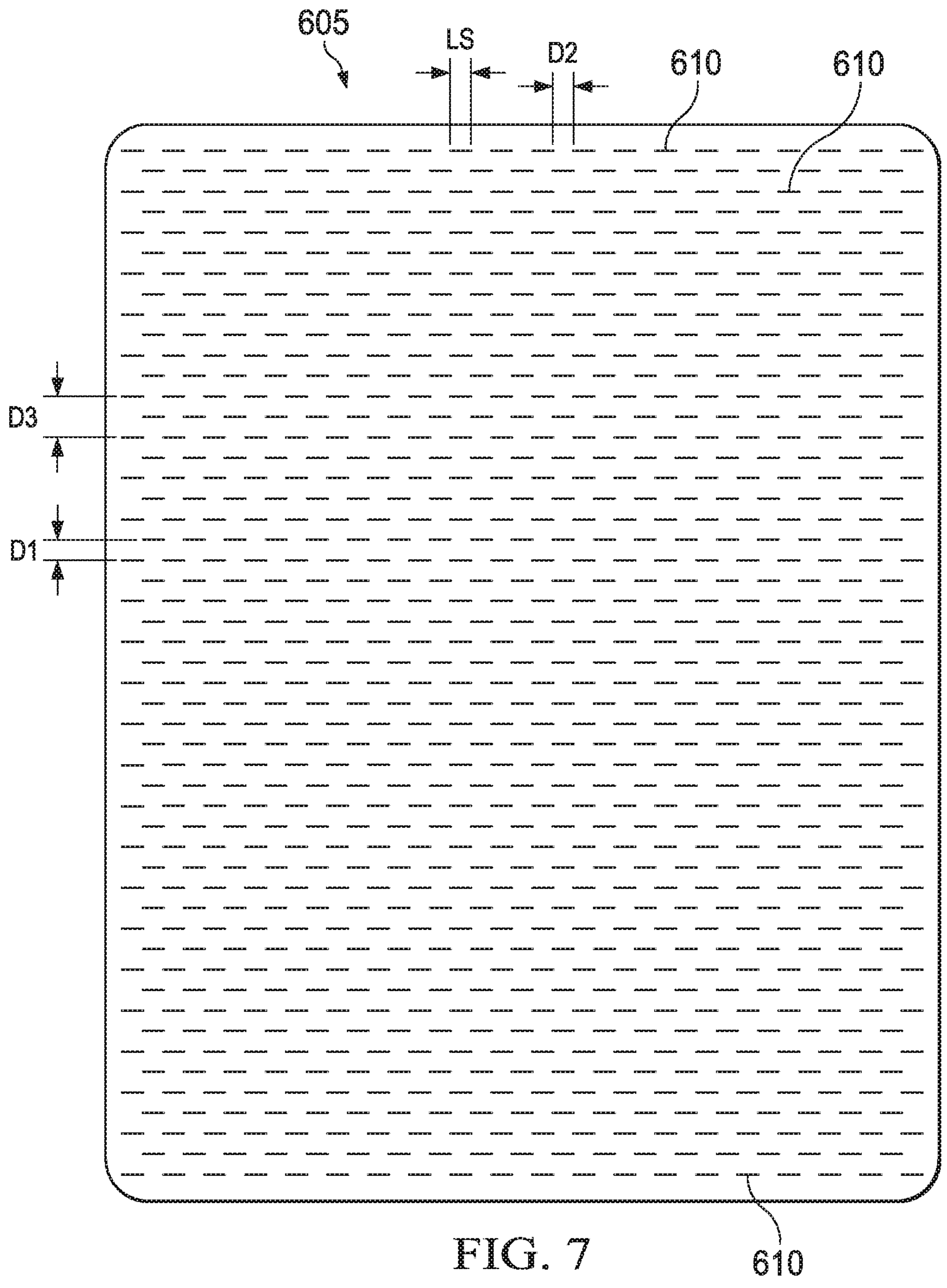
FIG. 7 is a schematic view of an example layer that can be associated with some embodiments of the dressing of FIG. 6.

FIG. 7 is a schematic view of another example of the fluid-control layer 605, illustrating additional details that may be associated with some embodiments. As illustrated in the example of FIG. 7, the perforations 610 may each consist essentially of one or more linear slots having a length LS. A length LS of about 3 millimeters may be suitable for some examples. FIG. 7 additionally illustrates an example of a uniform distribution pattern of the perforations 610. In FIG. 7, the perforations 610 are substantially coextensive with the fluid-control layer 605, and are distributed across the fluid-control layer 605 in a grid of parallel rows and columns, in which the slots are also mutually parallel to each other. The rows may be spaced a distance D1, and the perforations 610 within each of the rows may be spaced a distance D2. For example, a distance D1 of about 3 millimeters on center and a distance D2 of about 3 millimeters on center may be suitable for some embodiments. The perforations 610 in adjacent rows may be aligned or offset. For example, adjacent rows may be offset, as illustrated in FIG. 7, so that the perforations 610 are aligned in alternating rows separated by a distance D3. A distance D3 of about 6 millimeters may be suitable for some examples. The spacing of the perforations 610 may vary in some embodiments to increase the density of the perforations 610 according to therapeutic requirements.

Figure 8:
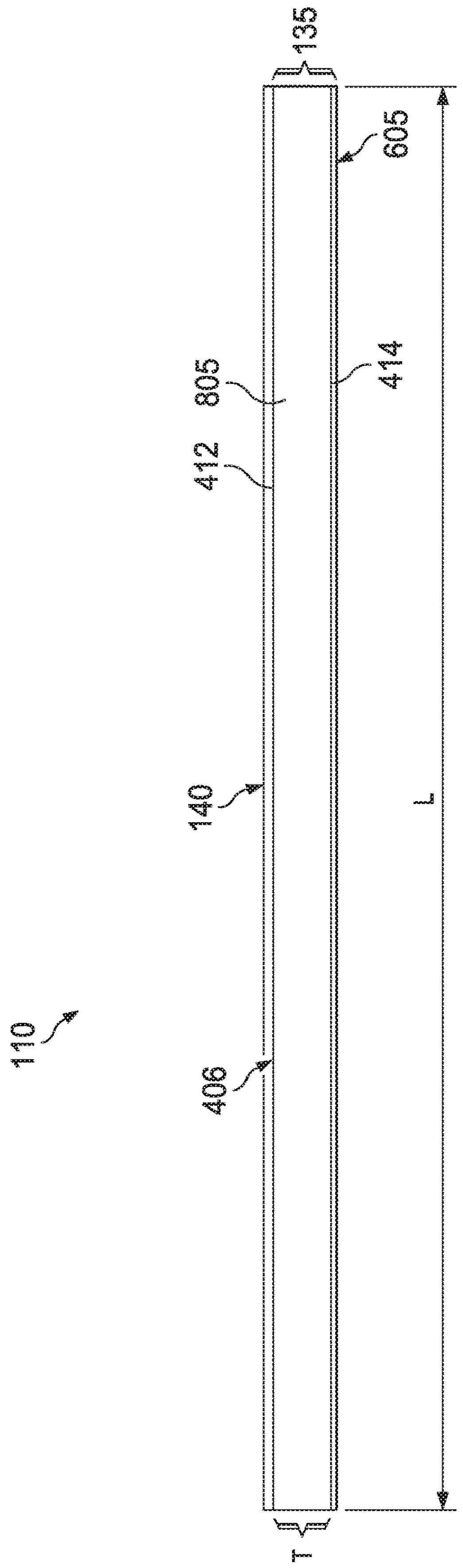
FIG. 8 is a side view of an example of the dressing of FIG. 6.

FIG. 8 is a side view of an example of the dressing 110 of FIG. 6 that may be associated with some embodiments of the therapy system of FIG. 1. As shown in FIG. 8, the tissue interface 135 may have an exposed perimeter 805. More particularly, in the example of FIG. 8, the cover 140, the fluid-control layer 605, and the manifold 406 each have an exposed perimeter, and there is no seam, weld, or seal along the exposed perimeter 805.

The manifold 406 generally has a first (planar) surface 414 and a second (planar) surface 412 opposite the first surface 414. The thickness T of the manifold 406 between the first surface 414 and the second surface 412 may also vary according to needs of a prescribed therapy. For example, the thickness T of the manifold 406 may be decreased to relieve stress on other layers and to reduce tension on peripheral tissue. The thickness of the manifold 406 can also affect the conformability and manifolding performance of the manifold 406. In some embodiments, a suitable foam may have a thickness T in a range of about 5 millimeters to 10 millimeters. In other examples, a suitable foam having a thickness Tin a range of about 6 millimeters to about 12 millimeters may be suitable, and a thickness T of at least 8 millimeters may be advantageous. Fabrics, including suitable 3D textiles and spacer fabrics, may have a thickness T in a range of about 2 millimeters to about 8 millimeters. The manifold 406 also has a length L, which can vary according needs of a particular tissue site or prescribed therapy.

In some embodiments, the fluid control layer 605 may be adjacent to the first surface 414 of the manifold 406, for example opposite the second surface 412. In some embodiments, the fluid control layer 1005 may be bonded to the first surface 414 of the manifold 406.

Figure 9:
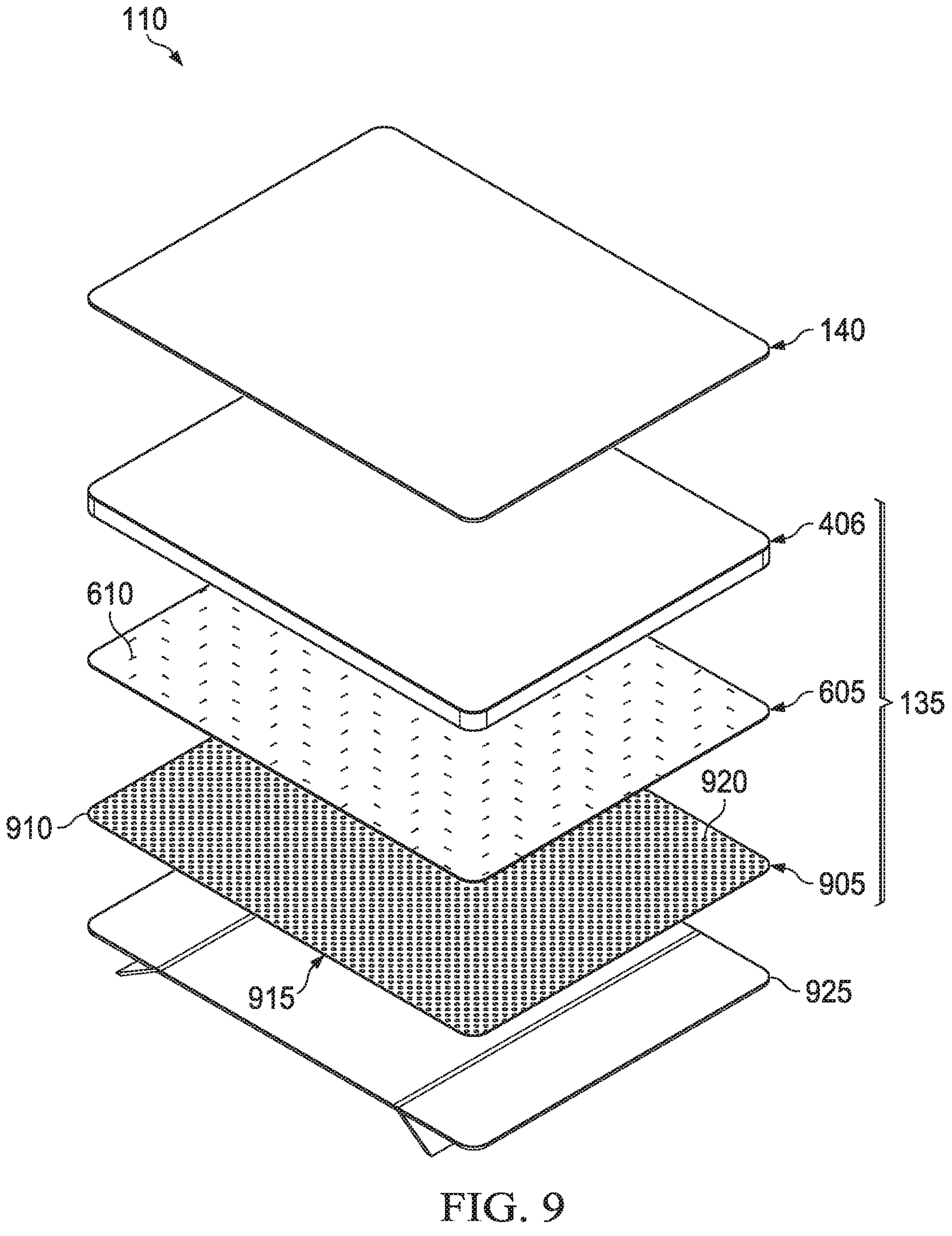
FIG. 9 is an exploded view of yet another example of a dressing that can be associated with some embodiments of the therapy system of FIG. 1.

FIG. 9 is an assembly view of still another example of the dressing 110 of FIG. 1, illustrating additional details that may be associated with some embodiments in which the tissue interface 135 may comprise additional layers. In the example of FIG. 9, the tissue interface 135 may optionally comprise a sealing layer 905, in addition to the fluid-control layer 605 and the manifold 406. In some embodiments, the sealing layer 905 may be adjacent to the fluid-control layer 605 opposite the manifold 406. The sealing layer 905 may also be bonded to the fluid-control layer 605 in some embodiments.

The sealing layer 905 may comprise or consist essentially of a sealing layer formed from a soft, pliable material, such as a tacky gel, suitable for providing a fluid seal with a tissue site, and may have a substantially flat surface. For example, the sealing layer 905 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. The sealing layer 905 may include an adhesive surface on an underside and a patterned coating of acrylic on a top side. The patterned coating of acrylic may be applied about a peripheral area to allow higher bonding in regions that are likely to be in contact with skin rather than the wound area. In other embodiments, the sealing layer 905 may comprise a low-tack adhesive layer instead of silicone. In some embodiments, the sealing layer 905 may have a thickness between about 200 microns (μm) and about 1000 microns (μm). In some embodiments, the sealing layer 905 may have a hardness between about 5 Shore OO and about 80 Shore OO. Further, the sealing layer 905 may be comprised of hydrophobic or hydrophilic materials.

In some embodiments, the sealing layer 905 may be a hydrophobic-coated material. For example, the sealing layer 905 may be formed by coating a porous material, such as, for example, woven, nonwoven, molded, or extruded mesh with a hydrophobic material. The hydrophobic material for the coating may be a soft silicone, for example.

The sealing layer 905 may have corners 910 and edges 915. The sealing layer 905 may include apertures 920. The apertures 920 may be formed by cutting or by application of local RF or ultrasonic energy, for example, or by other suitable techniques for forming an opening. The apertures 920 may have a uniform distribution pattern, or may be randomly distributed on the sealing layer 905. The apertures 920 in the sealing layer 905 may have many shapes, including circles, squares, stars, ovals, polygons, slits, complex curves, rectilinear shapes, triangles, for example, or may have some combination of such shapes.

Each of the apertures 920 may have uniform or similar geometric properties. For example, in some embodiments, each of the apertures 920 may be circular apertures, having substantially the same diameter. In some embodiments, the diameter of each of the apertures 920 may be between about 1 millimeter and about 50 millimeters. In other embodiments, the diameter of each of the apertures 920 may be between about 1 millimeter and about 20 millimeters.

In other embodiments, geometric properties of the apertures 920 may vary. For example, the diameter of the apertures 920 may vary depending on the position of the apertures 920 in the sealing layer 905. The apertures 920 may be spaced substantially equidistant over the sealing layer 905. Alternatively, the spacing of the apertures 920 may be irregular.

As illustrated in the example of FIG. 9, some embodiments of the dressing 110 may include a sealing layer release liner 925 to protect the sealing layer 905 prior to use. The sealing layer release liner 925 may also provide stiffness to facilitate handling and applying the dressing 110. The sealing layer release liner 925 may be similar to the release liner 428 in some embodiments. The sealing layer release liner 925 may be, for example, a casting paper, a film, or polyethylene. Further, in some embodiments, the sealing layer release liner 925 may be a polyester material such as polyethylene terephthalate (PET), or similar polar semi-crystalline polymer. The use of a polar semi-crystalline polymer for the sealing layer release liner 925 may substantially preclude wrinkling or other deformation of the dressing 110. For example, the polar semi-crystalline polymer may be highly orientated and resistant to softening, swelling, or other deformation that may occur when brought into contact with components of the dressing 110, or when subjected to temperature or environmental variations, or sterilization. Further, a release agent may be disposed on a side of the sealing layer release liner 925 that is configured to contact the sealing layer 905. For example, the release agent may be a silicone coating and may have a release factor suitable to facilitate removal of the sealing layer release liner 925 by hand and without damaging or deforming the dressing 110. In some embodiments, the release agent may be a fluorocarbon or a fluorosilicone, for example. In other embodiments, the sealing layer release liner 925 may be uncoated or otherwise used without a release agent.

Figure 10:
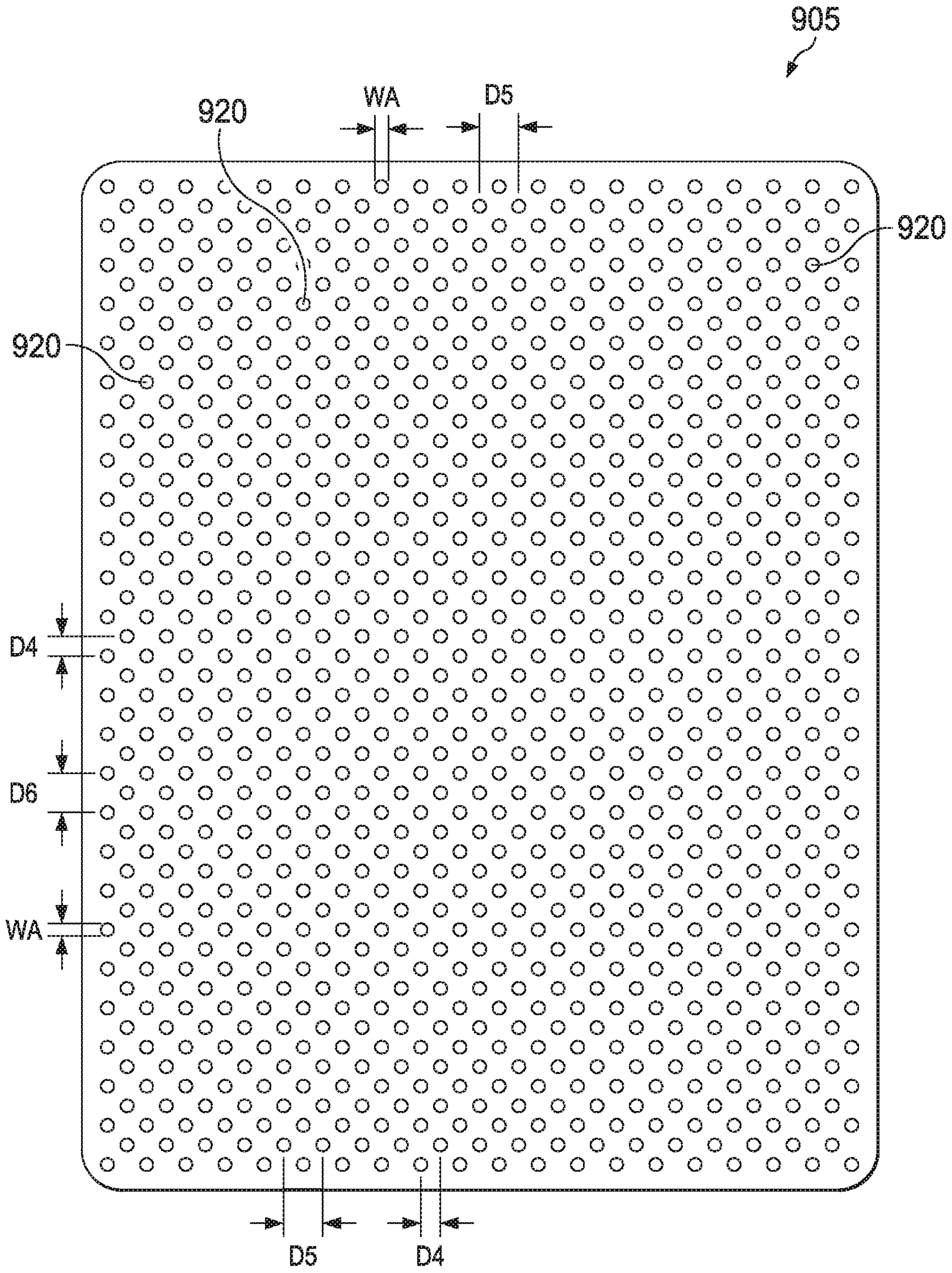
FIG. 10 is a schematic view of an example layer that can be associated with some embodiments of the dressing of FIG. 9.

FIG. 10 is a schematic view of an example configuration of the apertures 920, illustrating additional details that may be associated with some embodiments of the sealing layer 905. In some embodiments, the apertures 920 illustrated in FIG. 10 may be associated only with an interior portion of the sealing layer 905. In the example of FIG. 10, the apertures 920 are generally circular and have a width WA, which may be about 2 millimeters in some examples. FIG. 10 also illustrates an example of a uniform distribution pattern of the apertures 920. In FIG. 10, the apertures 920 are distributed across the sealing layer 905 in a grid of parallel rows and columns. Within each row and column, the apertures 920 may be equidistant from each other, as illustrated in the example of FIG. 10. The rows may be spaced a distance D4, and the apertures 920 within each of the rows may be spaced a distance D5. For example, a distance D4 of about 3 millimeters on center and a distance D5 of about 3 millimeters on center may be suitable for some embodiments. The apertures 920 in adjacent rows may be aligned or offset. For example, adjacent rows may be offset, as illustrated in FIG. 10, so that the apertures are aligned in alternating rows separated by a distance D6. A distance D6 of about 6 millimeters may be suitable for some examples. The spacing of the apertures 920 may vary in some embodiments to increase the density of the apertures 920 according to therapeutic requirements.

Figure 11:
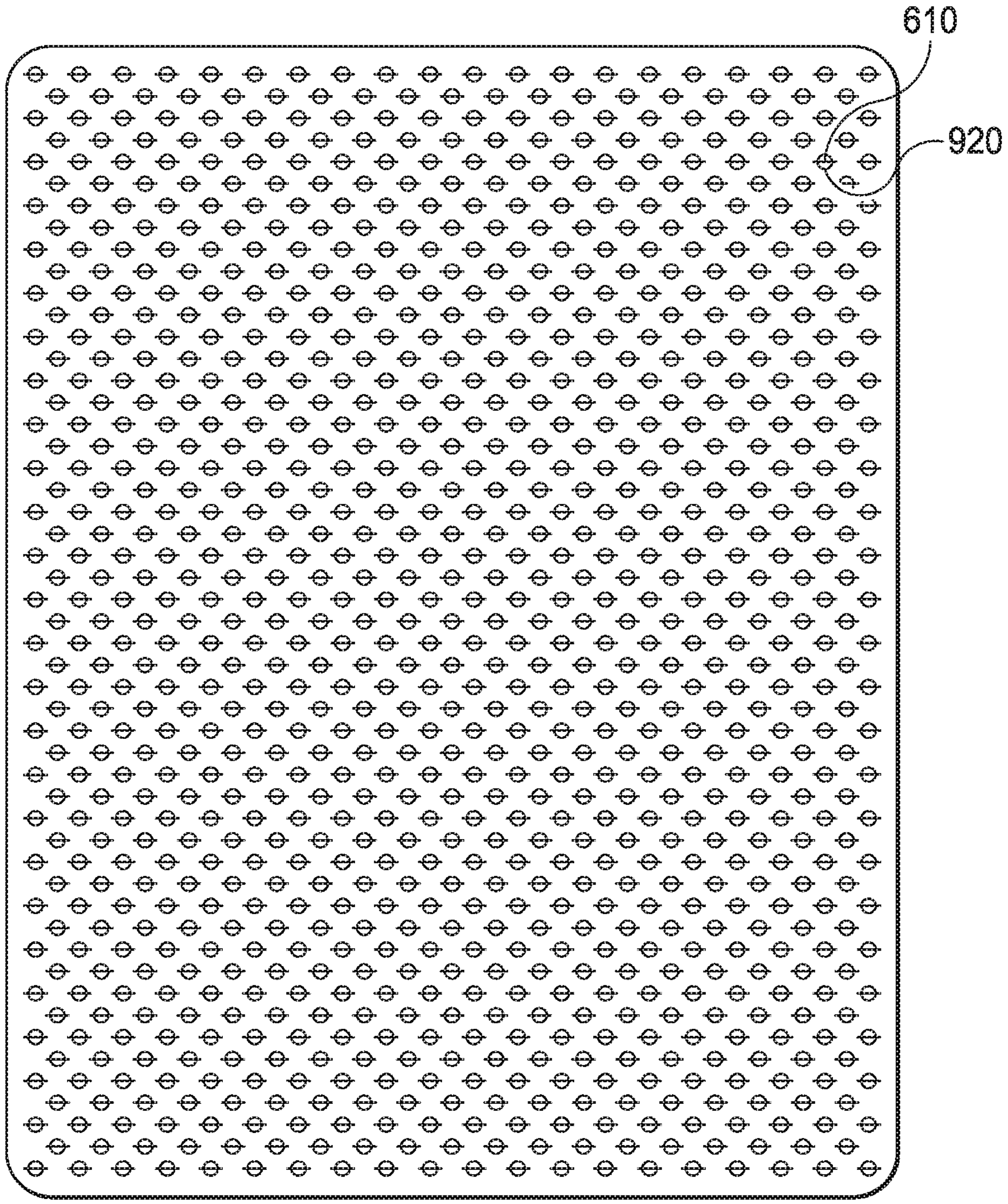
FIG. 11 is a schematic view of the example layer of FIG. 10 overlaid on the example layer of FIG. 7.

FIG. 11 is a schematic view of the sealing layer 905 of FIG. 10 overlaid on the fluid-control layer 605 of FIG. 7, illustrating additional details that may be associated with some example embodiments of the tissue interface 135. For example, as illustrated in FIG. 11, the perforations 610 may be aligned, overlapping, in registration with, or otherwise fluidly coupled to the apertures 920 in some embodiments. In some embodiments, one or more of the perforations 610 may be registered with the apertures 920 only in an interior portion, or only partially registered with the apertures 920. The perforations 610 in the example of FIG. 11 are generally configured so that each of the perforations 610 is registered with only one of the apertures 920. In other examples, one or more of the perforations 610 may be registered with more than one of the apertures 920. For example, any one or more of the perforations 610 may extend across two or more of the apertures 920. Additionally or alternatively, one or more of the perforations 610 may not be registered with any of the apertures 920.

As illustrated in the example of FIG. 11, the apertures 920 may be sized to expose a portion of the fluid-control layer 605, the perforations 610, or both through the sealing layer 905. In some embodiments, one or more of the apertures 920 may be sized to expose more than one of the perforations 610. For example, some or all of the apertures 920 may be sized to expose two or three of the perforations 610. In some examples, the length of each of the perforations 610 may be substantially equal to the diameter of each of the apertures 920. More generally, the average dimensions of the perforations are substantially similar to the average dimensions of the apertures 920. For example, the apertures 920 may be elliptical in some embodiments, and each of the perforations 610 may have a length LS that is substantially equal to the major axis or the minor axis of the ellipse. In some embodiments, the dimensions of the perforations 610 may exceed the dimensions of the apertures 920, and the size of the apertures 920 may limit the effective size of the perforations 610 exposed through the sealing layer 905.

Figure 12:
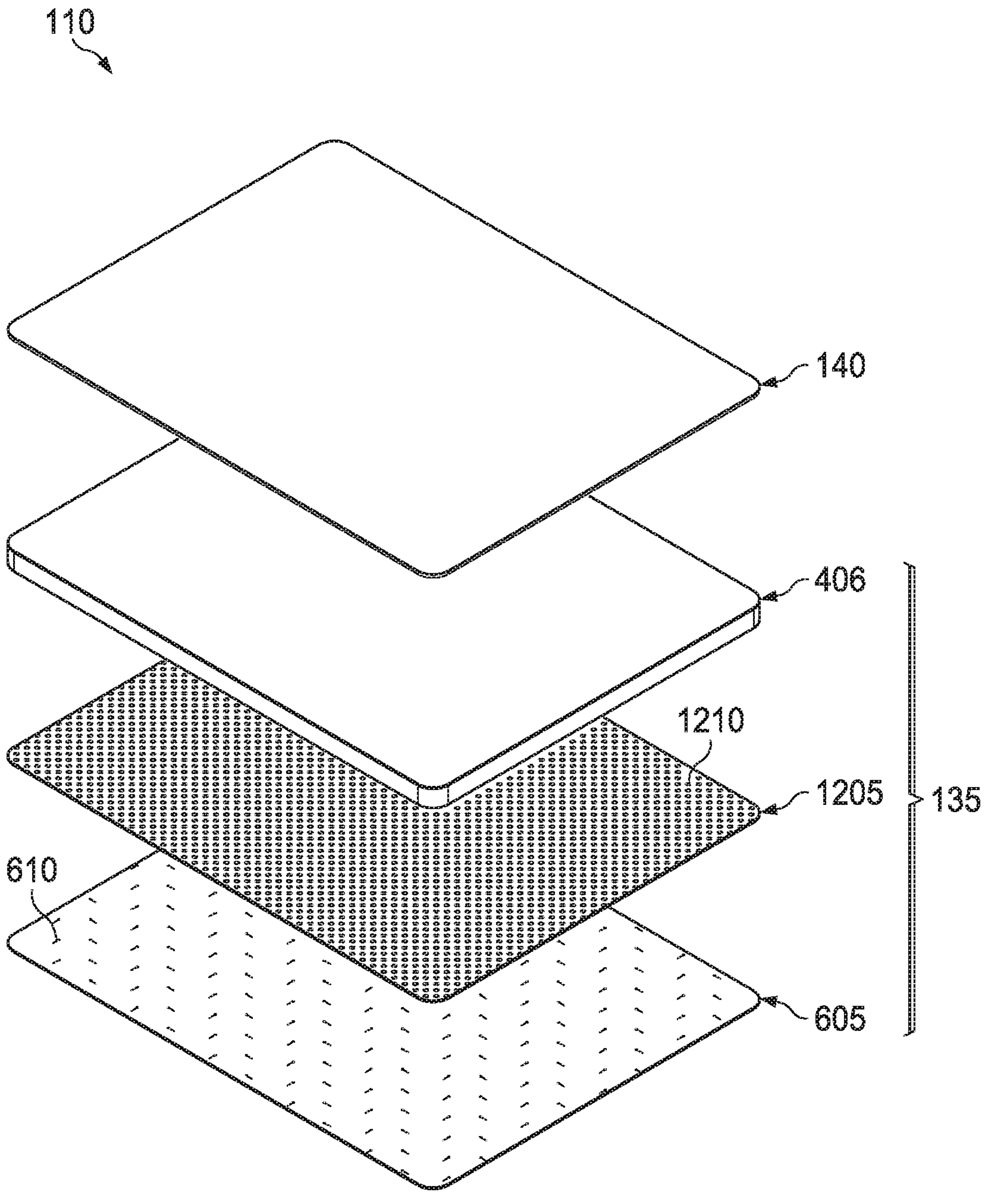
FIG. 12 is an exploded view of another example of a dressing that may be associated with some embodiments of the therapy system of FIG. 1.

FIG. 12 is an exploded view of yet another example of the dressing 110, illustrating additional details that may be associated with some example embodiments of the therapy system of FIG. 1. In the example of FIG. 12, the tissue interface 135 comprises a tie layer 1205 in addition to the fluid-control layer 605 and the manifold 406. The tie layer 1205 may have perforations 1210 and may have a thickness between 10 microns and 100 microns in some embodiments. The tie layer 1205 may be clear, colored, or printed. As illustrated in FIG. 12, the tie layer 1205 may be disposed between the fluid-control layer 605 and the manifold 406. The tie layer 1205 may also be bonded to at least one of the fluid-control layer 605 and the manifold 406 in some embodiments.

The tie layer 1205 may comprise polyurethane film, for example, which can be bonded to the fluid-control layer 605 and the manifold 406. For example, if the fluid-control layer 605 is formed of a polyethylene film and the manifold 406 is polyurethane foam, the fluid-control layer 605 may be more readily bonded to the tie layer 1205 than directly to the manifold 406.

In some embodiments, one or more of the components of the dressing 110 may additionally be treated with an antimicrobial agent. For example, the manifold 406 may be a foam, mesh, or non-woven coated with an antimicrobial agent. In some embodiments, the manifold 406 may comprise antimicrobial elements, such as fibers coated with an antimicrobial agent. Additionally or alternatively, some embodiments of the fluid-control layer 605 may be a polymer coated or mixed with an antimicrobial agent. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the manifold 406 may be foam coated with such a mixture.

The cover 140, the fluid-control layer 605, the manifold 406, the sealing layer 905, or various combinations may be assembled before application or in situ. For example, the fluid-control layer 605 may be laminated to the manifold 406, and the cover 140 may be laminated to the manifold 406 opposite the fluid-control layer 605 in some embodiments. The sealing layer 905 may also be coupled to the fluid-control layer 605 opposite the manifold 406 in some embodiments. In some embodiments, one or more layers of the tissue interface 135 may coextensive. For example, the fluid-control layer 605 and the manifold 406 may be cut flush with the edge of the cover 140, exposing the edge of the manifold 406. In other embodiments, the fluid-control layer 605 may overlap the edge of the manifold 406. In other embodiments, one or more layers of the dressing 110 may be applied at the tissue site, for example with the dressing 110 not fully assembled until placement at the tissue site. For example, the tissue interface 135 layers may be pre-assembled, but a separate cover may be applied over the tissue interface 135 as the dressing 110 is applied to the tissue site.

Figure 13:
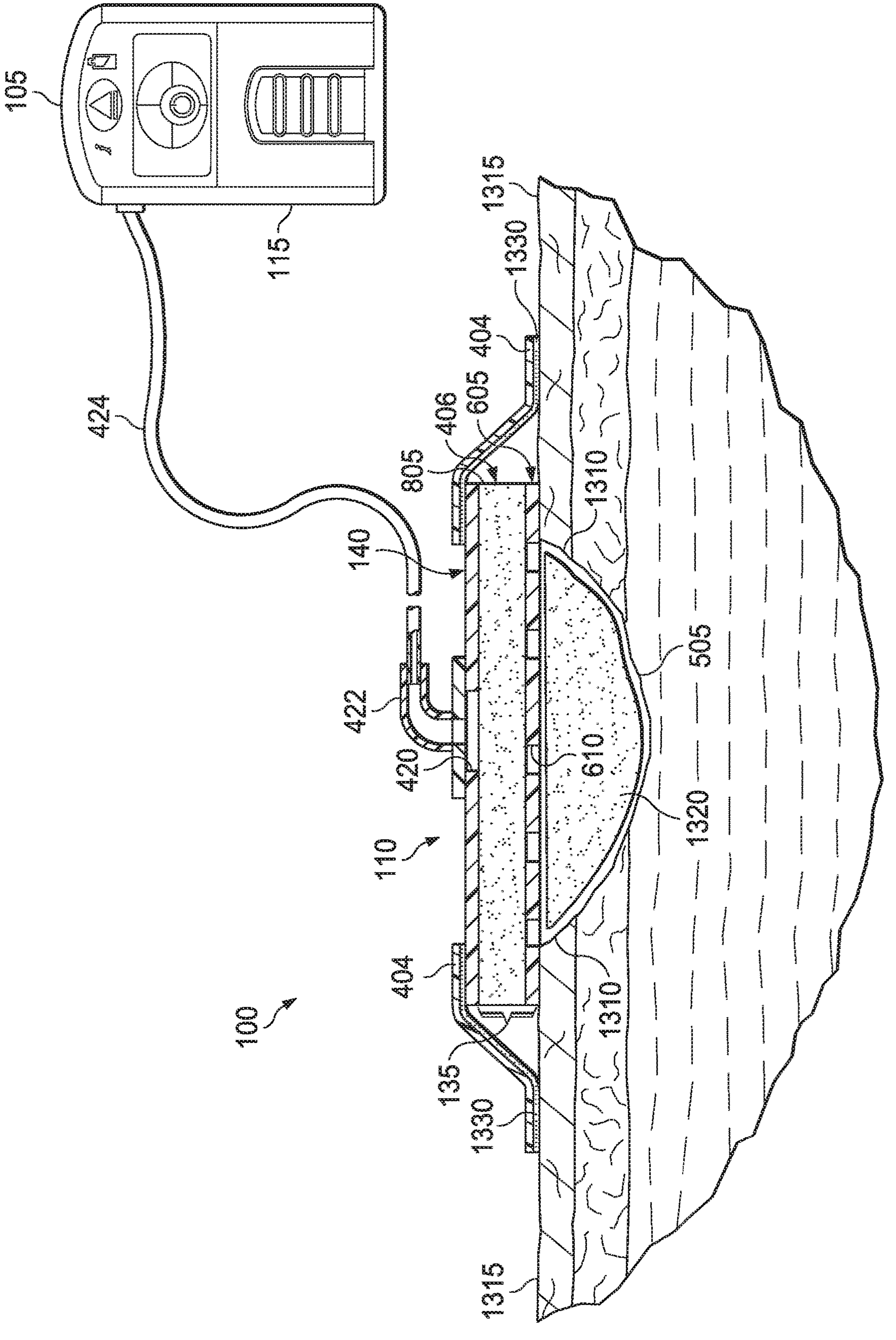
FIG. 13 is a schematic diagram of an example of the therapy system of FIG. 1 applied to a tissue site.

FIG. 13 is a schematic diagram of an example of the therapy system 100 applied to an exemplary tissue site 505. In the example of FIG. 13, the tissue site 505 is a surface wound. In use, a release liner (if included) may be removed to expose the tissue interface 135. The geometry and dimensions of the tissue interface 135, the cover 140, or both may vary to suit a particular application or anatomy. For example, the dressing 110 may be cut to size for a specific region or anatomical area, such as for amputations. The dressing 110 may be cut without losing pieces of the tissue interface 135 and without separation of the tissue interface 135.

The tissue interface 135 can be placed within, over, on, or otherwise proximate to the tissue site 505. In the example of FIG. 13, the fluid-control layer 605 forms an outer surface (e.g. the tissue-contact surface) of the dressing 110, and can be placed over the tissue site 505, including the edge 1310 and epidermis 1315. The fluid-control layer 605 may be interposed between the manifold 406 and the tissue site 505, which can prevent direct contact between the manifold 406 and epidermis 1315. In other examples, the sealing layer 905 may form an outer surface of the dressing 110 and can provide temporary fixation over the tissue site 505.

As illustrated in the example of FIG. 13, in some applications a filler 1320 may also be disposed between the tissue site 505 and the fluid-control layer 605. For example, if the tissue site is a surface wound, the filler 1320 may be applied interior to the edge 1310, and the fluid-control layer 605 may be disposed over the filler 1320. In some embodiments, the filler 1320 may be a manifold, such as open-cell foam. The filler 1320 may comprise or consist essentially of the same material as the manifold 406 in some embodiments.

In some examples, the dressing 110 may include one or more attachment devices 404. In some embodiments, one or more of the attachment devices 404 may comprise or consist essentially of a polymer strip, such as a polyurethane strip, having an adhesive 1330 thereon. In some examples the adhesive 1330 may be, for example, a medically-acceptable, pressure-sensitive adhesive that extends about a periphery, a portion, or an entire surface of each of the attachment devices 404. In some embodiments, for example, the adhesive 1330 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 1330 may be continuous or discontinuous. Discontinuities in the adhesive 1330 may be provided by apertures or holes (not shown) in the adhesive 1330. The apertures or holes in the adhesive 1330 may be formed after application of the adhesive 1330 or by coating the adhesive 1330 in patterns on a carrier layer, such as, for example, a side of the attachment devices 404. Apertures or holes in the adhesive 1330 may also be sized to enhance the MVTR of the attachment devices 404 in some example embodiments. In some embodiments, one or more of the attachment devices 404 may comprise or consist essentially of a composite strip of a perforated gel, substantially similar to the sealing layer 905, and a backing with an adhesive.

The attachment devices 404 can be disposed around edges of the cover 140, and the adhesive may pressed onto the cover 140 and epidermis 1315 (or other attachment surface) to fix the dressing 110 in position and to seal the exposed perimeter 805 of the manifold 406.

FIG. 13 also illustrates one example of a fluid conductor 424 and a dressing interface 422. As shown in the example of FIG. 9, the fluid conductor 424 may be a flexible tube, which can be fluidly coupled on one end to the dressing interface 422. The dressing interface 422 may be an elbow connector, as shown in the example of FIG. 9. In some examples, the tissue interface 135 can be applied to the tissue site 505 before the cover 140 is applied over the tissue interface 135. The cover 140 may include a port 420, or the port 420 may be cut into the cover 140 before or after positioning the cover 140 over the tissue interface 135. The port 420 of FIG. 13 is centrally disposed. In other examples, the position of the port 420 may be off-center or adjacent to an end or edge of the cover 140. The dressing interface 422 can be placed over the port 420 to provide a fluid path between the fluid conductor 424 and the tissue interface 135.

In other examples, the fluid conductor 424 may be inserted directly through the cover 140 into the tissue interface 135.

If not already configured, the dressing interface 422 may be disposed over the port 420 and attached to the cover 140. The fluid conductor 424 may be fluidly coupled to the dressing interface 422 and to the negative-pressure source 105.

Negative pressure from the negative-pressure source 105 can be distributed through the fluid conductor 424 and the dressing interface 422 to the tissue interface 135. Negative pressure applied through the tissue interface 135 can also create a negative pressure differential across the perforations 610 in the fluid-control layer 605, which can open or expand the perforations 610. For example, in some embodiments in which the perforations 610 may comprise substantially closed fenestrations through the fluid-control layer 605, a pressure gradient across the fenestrations can strain the adjacent material of the fluid-control layer 605 and increase the dimensions of the fenestrations to allow liquid movement through them, similar to the operation of a duckbill valve. Opening the perforations can allow exudate and other liquid movement through the perforations into the manifold 406. The manifold 406 can provide passage of negative pressure and exudate, which can be collected in the container 115.

Changes in pressure can also cause the manifold 406 to expand and contract. The fluid-control layer 605 can protect the epidermis 1315 from irritation that could be caused by expansion, contraction, or other movement of the manifold 406. The fluid-control layer 605 can also substantially reduce or prevent exposure of a tissue site to the manifold 406, which can inhibit growth of tissue into the manifold 406.

If the negative-pressure source 105 is removed or turned off, the pressure differential across the perforations 610 can dissipate, allowing the perforations 610 to close and prevent exudate or other liquid from returning to the tissue site 505 through the fluid-control layer 605.

Additionally, or alternatively, instillation solution or other fluid may be distributed to the dressing 110, which can increase the pressure in the tissue interface 135. The increased pressure in the tissue interface 135 can create a positive pressure differential across the perforations 610 in the fluid-control layer 605, which can open the perforations 610 to allow the instillation solution or other fluid to be distributed to the tissue site 505.

Figure 14:
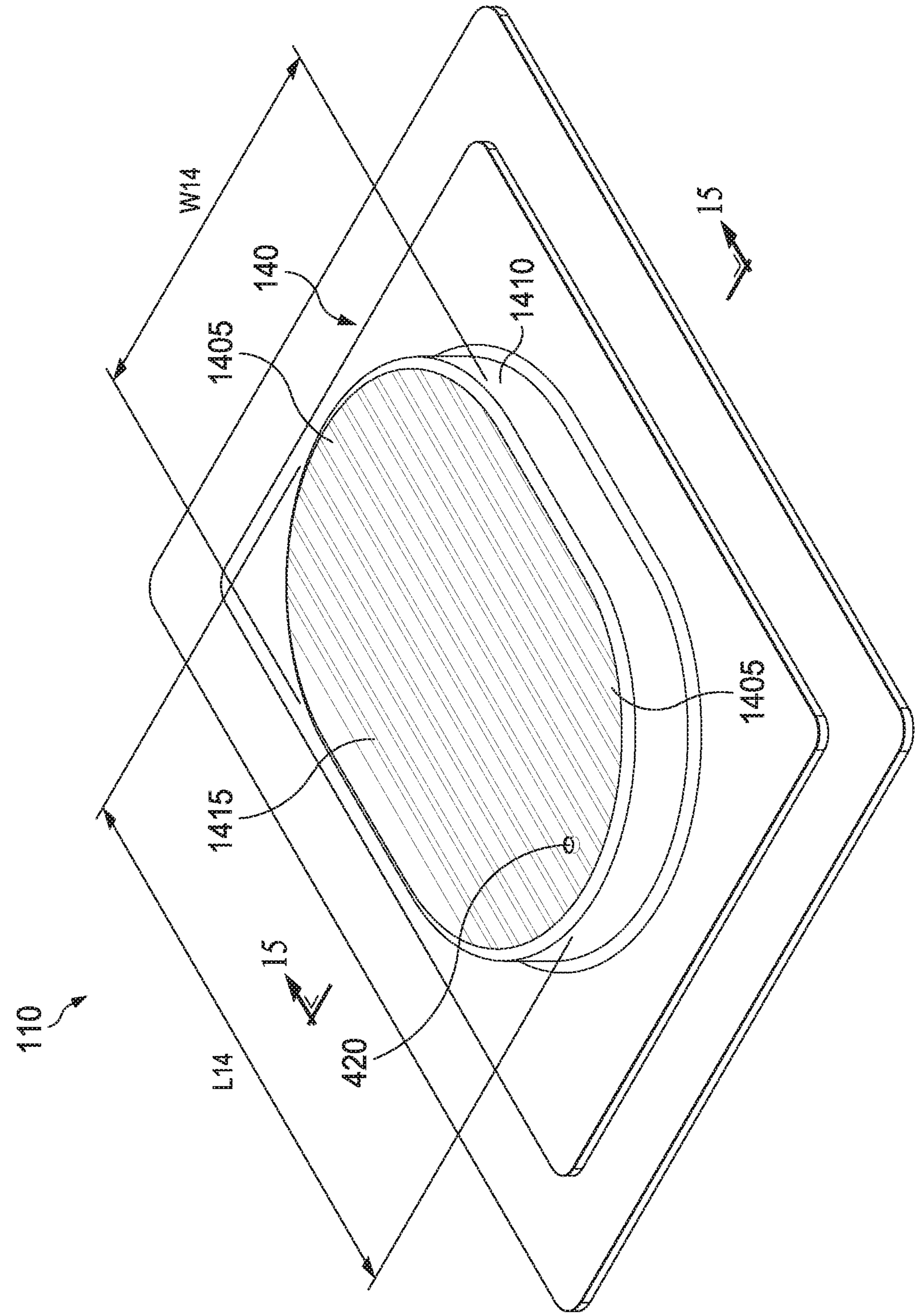
FIG. 14 is an isometric view of yet another exemplary dressing with fluid transport features on the top cap portion of the interior surface of the cover.
Figure 15:
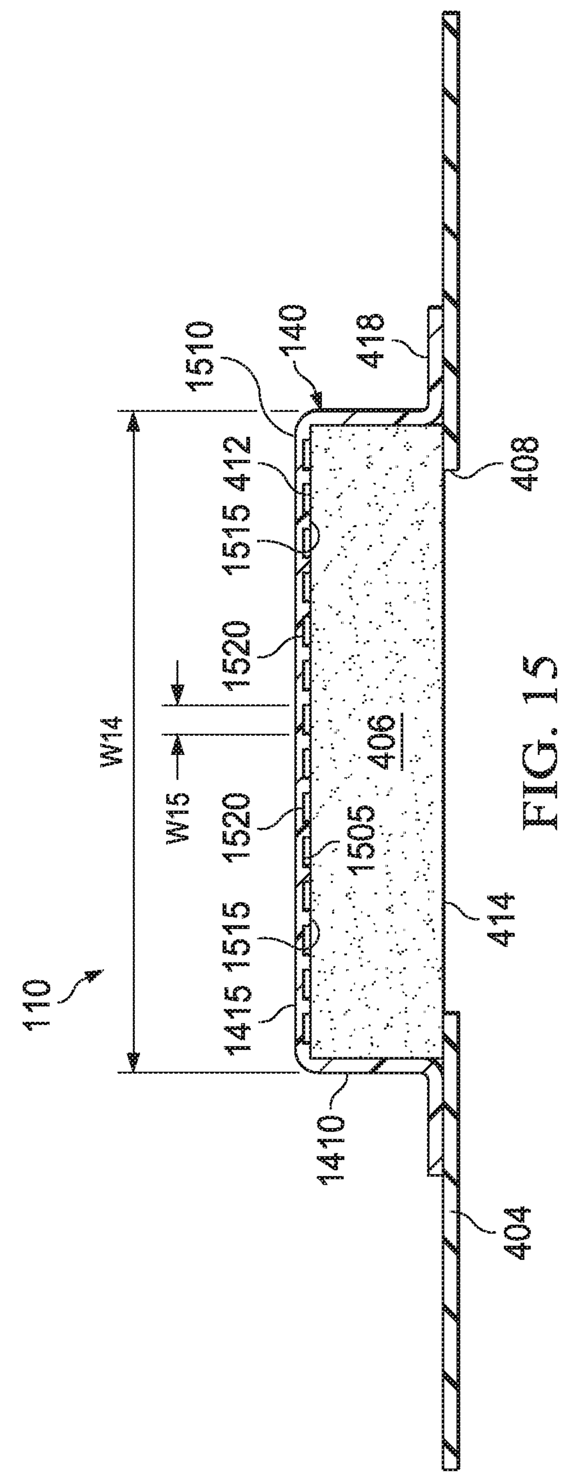
FIG. 15 is a cross-section view of the dressing of FIG. 14.

FIGS. 14-15 show yet another exemplary dressing 110, illustrating additional details that may be associated with some example embodiments of the therapy system of FIG. 1. FIGS. 14-15 may illustrate an exemplary dressing 110 similar to that of FIG. 4 that also has a plurality of fluid transport features 1405 (which may also be interchangeably termed exudate transport features or liquid channeling features) on an interior surface 1505 of the cover 140. For example, the dressing 110 may comprise the manifold 406 having the first surface 414 and the second surface 412; and the cover 140 configured to be disposed over the manifold 406. In some embodiments, the manifold 406 may be configured to distribute negative pressure, for example with negative pressure applied to the dressing 110 being distributed substantially throughout the manifold 406. In some embodiments, the first surface 414 of the manifold 406 may be configured to face towards the tissue site, and the second surface 412 of the manifold 406 may be configured to be opposite the first surface 414 (e.g. separated by the thickness of the manifold 406) and to face away from the tissue site. In some embodiments, the cover 140 may comprise the interior surface 1505 configured so that at least a portion (e.g. a top cap portion) of the interior surface 1505 faces towards the second surface 412 of the manifold 406 (and/or the tissue site), an exterior surface 1510 (for example, opposite the interior surface 1505 and/or configured to face away from the manifold 406 and/or the tissue site), and a plurality of fluid transport features 1405 on at least a portion of the interior surface 1505. In some embodiments, the fluid transport features 1405 may be configured to permit or provide directional control of fluid along channels for transfer of fluid from one portion of the dressing 110 to another portion of the dressing 110. In some embodiments, the exterior surface 1510 may be substantially flat or smooth (e.g. without projections or indentations, such as the fluid transport features).

In some embodiments, at least a portion of the fluid transport features 1405 may be configured for capillary action (e.g. capillary movement of liquid). For example, at least a portion of the fluid transport features 1405 may be configured to wick fluid across the interior surface 1505 of the cover 140 by capillary action. In some embodiments, the fluid transport features 1405 may be configured to transport fluid the length L14 of the manifold 406 via capillary action. Capillarity may be the action (e.g. occurring because of intermolecular forces between the liquid and surrounding solid surfaces) by which the surface of a liquid, where it is in contact with a solid (as in a capillary tube), is elevated or depressed depending on the relative attraction of the molecules of the liquid for each other and for those of the solid. Capillary action may allow movement, for example due to the forces of adhesion, cohesion, and surface tension, of a liquid along a surface of a solid caused by the attraction of molecules of the liquid to the molecules of the solid. In effect, capillary action may allow a liquid to flow in narrow spaces without the assistance of, or even in opposition to, external forces like gravity. In some embodiments, the plurality of fluid transport features 1405 may comprise a plurality of channels (e.g. micro-channels) sized for capillary action. For example, the channels sized for capillary action may have a width of approximately 5-3000 micron and/or a depth of approximately 5-3000 micron, a width of approximately 25-3000 micron and/or a depth of approximately 25-3000 micron, a width of approximately 50-3000 micron and/or a depth of approximately 50-3000 micron, a width of approximately 350-3000 micron and/or a depth of approximately 350-3000 micron, or a width of approximately 5-350 micron and/or a depth of approximately 5-350 micron. In some embodiments, the width and depth of the channels may be approximately equal.

In some embodiments, the fluid transport features 1405 may comprise micro-molded features, for example a micro-molded pattern of projections on the interior surface 1505 of the cover 140. In some embodiments, the interior surface 1505 of the cover 140 may be formed by a film incorporating a micro-replicated pattern. In some embodiments, the fluid transport features 1405 may be configured to allow fluid movement (e.g. longitudinally) through the dressing 110 even when negative pressure cannot be effectively dispersed through the manifold 406. For example, the fluid transport features 1405 may allow fluid movement within the dressing 110 even when the manifold 406 is clogged and/or even when the negative-pressure differential is insufficient for fluid movement. In some embodiments, the fluid transport features 1405 may be configured to improve vertical transport of fluid through the dressing 110, for example longitudinal transport when the dressing 110 is oriented vertically. For example, the fluid transport features 1405 may be configured to assist in overcoming a fluid head caused by vertical orientation of the dressing 110.

In some embodiments, the dressing 110 may be configured with multiple fluid transport mechanisms. For example, in addition to fluid transport via negative pressure distribution in the manifold 406 (which typically may be the primary fluid transport mechanism for the negative-pressure dressing 110), the dressing 110 may also comprise one or more of the following fluid transport mechanisms: capillary action fluid transport via fluid transport features 1405 (such as channels) configured for capillary action and/or negative-pressure differential fluid transport between the manifold 406 and the cover 140 via fluid transport features 1405 (such as channels) configured to provide larger pathways relative to the smaller capillary action channels. In some embodiments, the dressing 110 may be configured so that the one or more additional fluid transport mechanism (e.g. the capillary action channels) may only operate in response to negative pressure within the manifold 406 falling to or below a pre-set level, for example due to clogging of the manifold 406 and/or a pressure head from fluid in a vertically-oriented dressing 110. In other embodiments, the one or more additional fluid transport mechanisms may operate simultaneously with negative pressure distribution through the manifold 406 (e.g. supplementing fluid transport through the dressing 110, for example to increase flow rate), but may become the primary fluid transport mechanism in response to negative pressure in the manifold 406 falling to or below the pre-set level. In some embodiments, the pre-set level may be approximately zero, for example with the manifold becoming substantially completely clogged. In some embodiments, the fluid transport features 1405 may ensure some level, for example at least a minimum flow rate, of fluid flow within the dressing 110, even if the manifold 406 becomes incapable of effective fluid flow. FIGS. 14-15 illustrate an example dressing 110 configured to provide only one additional fluid transport mechanism (since all the channels are similarly sized); the additional fluid transport mechanism may depend on the size and/or shape of the channels formed by the fluid transport features 1405. For example, the additional fluid transport mechanism in FIG. 14 may be capillary action, due to fluid transport features 1405 configured for capillary action.

In FIG. 14, the manifold 406 may be elongate, for example having a length L14 and a width W14, with the length L14 being greater than the width W14. In some embodiments, the fluid transport features 1405 (e.g. the channels) may be oriented to extend longitudinally. For example, the fluid transport features 1405 may extend substantially parallel to the length L14 of the manifold 406 and/or substantially perpendicular to the width W14 of the manifold 406. In some embodiments, the fluid transport features 1405 may extend approximately the length L14 of the manifold 406. Some embodiments may further comprise the port 420, which may be configured for introduction of negative pressure through the cover 140 and/or to the manifold 406. While in some embodiments, the port 420 may be an integral part of the cover 140 formed during the dressing 110 manufacturing process, in other embodiments, the port 420 may be formed in the cover 140 during the application process to the tissue site. In some embodiments, the port 420 may be located in proximity to one elongate end of the dressing 110. In some embodiments, the fluid transport features 1405 may be configured to allow and/or to facilitate longitudinal fluid movement within the dressing 110 towards the port 420. In some embodiments, the cover 140 may further comprise a plurality of sidewalls 1410 and a top cap 1415. For example, the top cap 1415 and the sidewalls 1410 may jointly envelop the manifold 406 on all sides except the first surface 414. In some embodiments, the port 420 may be located on the top cap 1415 of the cover 140. In some embodiments, the fluid transport features 1405 may be located on the top cap 1415. For example, in FIG. 14, the fluid transport features 1405 may substantially span (e.g. be coextensive with) the top cap 1415. In some embodiments, the fluid transport features 1405 may span only the top cap 1415, and may not extend on the sidewalls 1410. In some embodiments, the dressing 110 may be non-absorbent, for example with the tissue interface 135 not including any material that is substantially absorbent. In some embodiments, the non-absorbent dressing 110 may not include any superabsorbent material.

FIG. 15 is a cross-section view of the dressing 110 of FIG. 14, illustrating additional details that may be associated with some embodiments. In some embodiments, the plurality of fluid transport features 1405 may comprise a plurality of open channels, which may comprise a plurality of ridges 1515 and grooves 1520. For example, each channel may be formed by a groove 1520 located between two adjacent ridges 1515. In some embodiments, the ridges 1515 and/or grooves 1520 may be micro-molded features. In some embodiments, at least some of the grooves 1520 may have a width W15 configured to provide fluid transport via capillary action, even when negative pressure in the dressing 110 is insufficient to induce fluid transport. In some embodiments, all of the channels may be similarly sized (e.g. with a width W15 sized for capillary action) and may extend substantially parallel to each other. For example, the plurality of ridges 1515 may be substantially linear and may extend substantially parallel to each other, with the spacing between adjacent ridges 1515 being substantially uniform. In some embodiments, all of the ridges 1515 and all of the grooves 1520 may be substantially similar. For example, all of the ridges 1515 may be approximately the same height and/or width, and may be approximately equally spaced apart by width W15. In some embodiments, the height of the ridges 1515 may be approximately the same dimension as the width W15 of the grooves 1520. In some embodiments, the width W15 may be approximately 5-3000 micron, approximately 25-3000 micron, or approximately 5-350 micron.

As shown in FIG. 15, in some embodiments, the ridges 1515 and grooves 1520 may be disposed on the interior surface 1505 of the top cap 1415, and the interior surface 1505 of the sidewalls 1410 may be substantially smooth. In some embodiments, the ridges 1515 may contact the second surface 412 of the manifold 406. For example, the second surface 412 of the manifold 406 may contact the free end of the ridges 1515 to close-off the channels, forming capillary tubes. In some embodiments, the second surface 412 of the manifold 406 may contact the ridges 1515 but may not completely fill-in the grooves 1520 on the interior surface 1505. For example, the grooves 1520 may be configured to maintain an open capillary action pathway (e.g. by not allowing the manifold 406 to completely fill-in the grooves 1520), even when negative pressure is applied to the dressing 110. In some embodiments, the ridges 1515 may be sufficiently rigid, the grooves 1520 may be sufficiently deep and/or shaped, and/or the manifold 406 may be sufficiently firm (e.g. non-compliant) and/or have pores sufficiently large to avoid significant intrusion by the manifold 406 into the grooves 1520 under negative pressure. For example, there may be substantially no intrusion of the manifold 406 into the channels during negative-pressure therapy and/or the manifold 406 may not occlude the channels during negative-pressure therapy.

In some embodiments, the cover 140 (e.g. the interior surface 1505 of the cover 140) may contact the second surface 412 of the manifold 406. In some embodiments, at least a portion of the cover 140 may be attached to at least a portion of the manifold 406. In other embodiments, the cover 140 may not be directly attached to the manifold 406. For example, the cover 140 may not be attached to the second surface 412 of the manifold 406. In some embodiments, the cover 140 may encapsulate the manifold 406 on all sides except the first surface 414.

Some dressing 110 embodiments may further comprise an attachment device 404 configured to sealingly attach (e.g. adhere) the cover 140 to the tissue site. The attachment device 404 may be configured to interact with the cover 140 so as to attach the manifold 406 in place on the tissue site, for example by attaching the cover 140 when disposed over the manifold 406 to the tissue site. In some embodiments, the attachment device 404 may have a treatment aperture 408, and may be configured for the first surface 414 of the manifold 406 to be at least partially exposed to (e.g. facing and/or in fluid communication with) the tissue site through the treatment aperture 408. For example, the treatment aperture 408 may be smaller than the first surface 414 of the manifold 406, forming a lip around the perimeter of the first surface 414 of the manifold 406 which may contain or hold the manifold 406 within the cover 140 prior to attachment of the dressing 110 to the tissue site. In some embodiments, the treatment aperture 408 may be sized so that at least 90% of the first surface 414 of the manifold 406 is exposed through the treatment aperture 408. In some embodiments, the manifold 406 may be configured to be directly exposed to the tissue site through the treatment aperture 408 (e.g. with no intervening layer). In some embodiments, the manifold 406 may be configured to be indirectly exposed through the treatment aperture 408, for example facing the tissue site and in fluid communication with the tissue site through the treatment aperture 408, but with a sealing layer 905, a comfort layer or protective layer 425, and/or a fluid control layer 605 between the manifold 406 and the tissue site. In some embodiments, the cover 140 may further comprise a flange 418, and the attachment device 404 may be configured to attach the flange 418 to the tissue site. In some embodiments, the flange 418 of the cover 140 may attach to the attachment device 404. In some embodiments, the cover 140, the manifold 406, and the attachment device 404 may be pre-formed as an integral dressing 110 (e.g. configured for peel-and-place application to the tissue site).

In some embodiments, the cover 140 may comprise (e.g. be formed of) a polymer film that is substantially fluid impermeable. For example, the polymer film of the cover 140 may comprise polyurethane or polyethylene. In some embodiments, the manifold 406 may comprise open-cell or reticulated foam, such as polyurethane foam. Some dressing 110 embodiments may further comprise a protective layer (not shown here).

Figure 17:
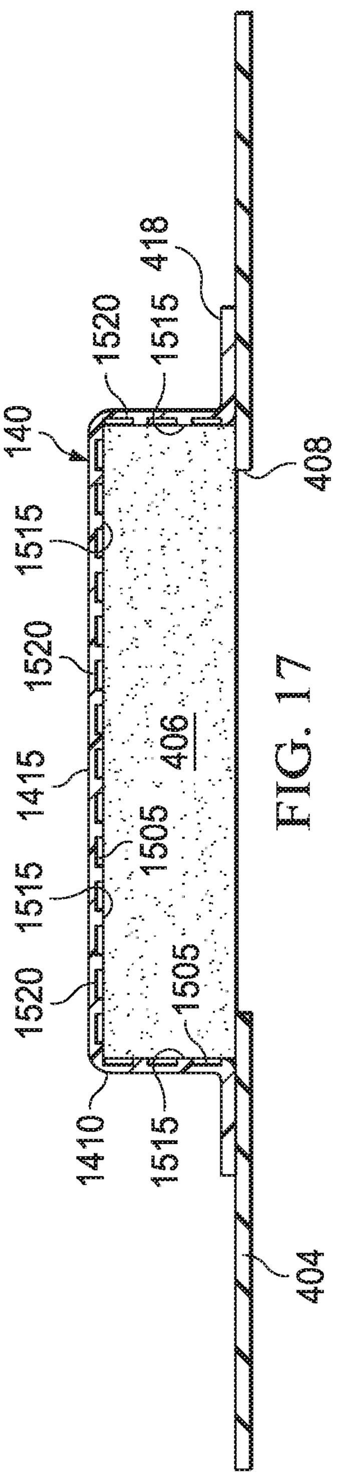
FIG. 17 is a cross-section view of the dressing of FIG. 16.
Figure 16:
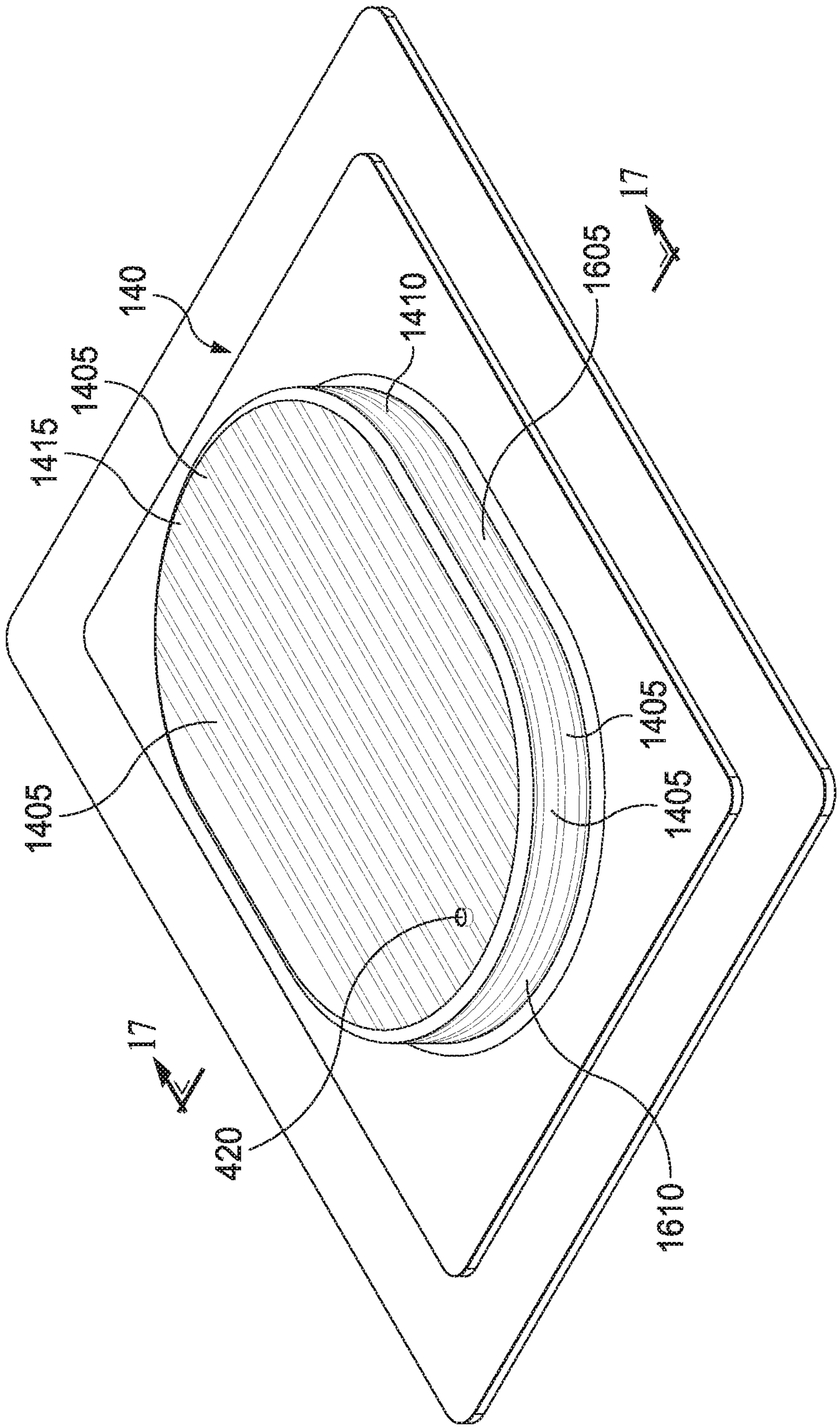
FIG. 16 is an isometric view of still another exemplary dressing with fluid transport features on the top cap and sidewalls of the cover.

FIGS. 16-17 show still another exemplary dressing 110, illustrating additional details that may be associated with some embodiments. FIG. 16 is an isometric view of the exemplary dressing 110, which may be similar to that of FIG. 14, illustrating an embodiment with additional fluid transport features 1405. In some embodiments, the plurality of sidewalls 1410 of the cover 140 may comprise two longitudinal sidewalls 1605 and two end sidewalls 1610. In some embodiments, the fluid transport features 1405 may also be located on (e.g. be coextensive with) at least the longitudinal sidewalls. In some embodiments, the fluid transport features 1405 may be located on (e.g. coextensive with) the interior surface 1505 of all of the sidewalls 1410, for example with the fluid transport features 1405 spanning the interior surface 1505 of the top cap 1415 and all sidewalls 1410 of the cover 140.

FIG. 17 is a cross-section view of the dressing 110 of FIG. 16, illustrating additional details that may be associated with some embodiments. In some embodiments, all of the channels on the interior surface 1505 of the cover 140 (e.g. spanning the top cap 1415 and all sidewalls 1410) may be similarly sized. In some embodiments, all of the channels on the top cap 1415 may extend substantially parallel, for example parallel to the length of the elongate manifold 406. In some embodiments, all of the channels on each sidewall 1410 may extend substantially parallel to each other. In some embodiments, the channels of the sidewalls 1410 may extend longitudinally. For example, the plurality of ridges 1515 on the top cap 1415 may be substantially linear and may extend substantially parallel to each other on the top cap 1415, with the spacing (e.g. the grooves 1520) between such adjacent ridges 1515 being substantially uniform; and the plurality of ridges 1515 on each of the sidewalls 1410 may be substantially linear and may extend substantially parallel to each other on the respective sidewall 1410, with the spacing (e.g. the grooves 1520) between such adjacent ridges 1515 being substantially uniform. In some embodiments, all of the ridges 1515 and all of the grooves 1520 on the cover 140 may be substantially similar. For example, all of the ridges 1515 may be approximately the same height, and may be approximately equally spaced apart. In some embodiments, the grooves 1520 may be sized for capillary action.

In some embodiments, the manifold 406 may contact the ridges 1515 (e.g. on the top cap and all sidewalls), but may not completely fill-in the grooves 1520 on the interior surface 1505. For example, the grooves 1520 may be configured to maintain an open capillary action pathway (e.g. by not allowing the manifold 406 to completely fill-in the grooves 1520), even when negative pressure is applied to the dressing 110. In some embodiments, the ridges 1515 may be sufficiently rigid, the grooves 1520 may be sufficiently deep and/or shaped, and/or the manifold 406 may be sufficiently firm (e.g. non-compliant) to avoid significant intrusion by the manifold 406 into the grooves 1520 under negative pressure. For example, there may be substantially no intrusion of the manifold 406 into the channels during negative-pressure therapy. In some embodiments, the interaction of the manifold with the ridges 1515 may form enclosed capillary action channels.

In some embodiments, the flange 418 of the cover 140 may not include any fluid transport features 1405. For example, the flange 418 may have a substantially flat interior surface 1505. In some embodiments, the interior surface 1505 of the flange 418 may contact and/or attach to the attachment device 404 (e.g. around the treatment aperture 408). As shown in FIG. 17, the fluid transport features 1405 may be substantially coextensive with the interior surface 1505 of the cover 140 except for the flange 418. For example, the fluid transport features 1405 may be disposed along the portion of the interior surface 1505 of the cover 140 contacting or adjacent to the manifold 406.

Figure 18:
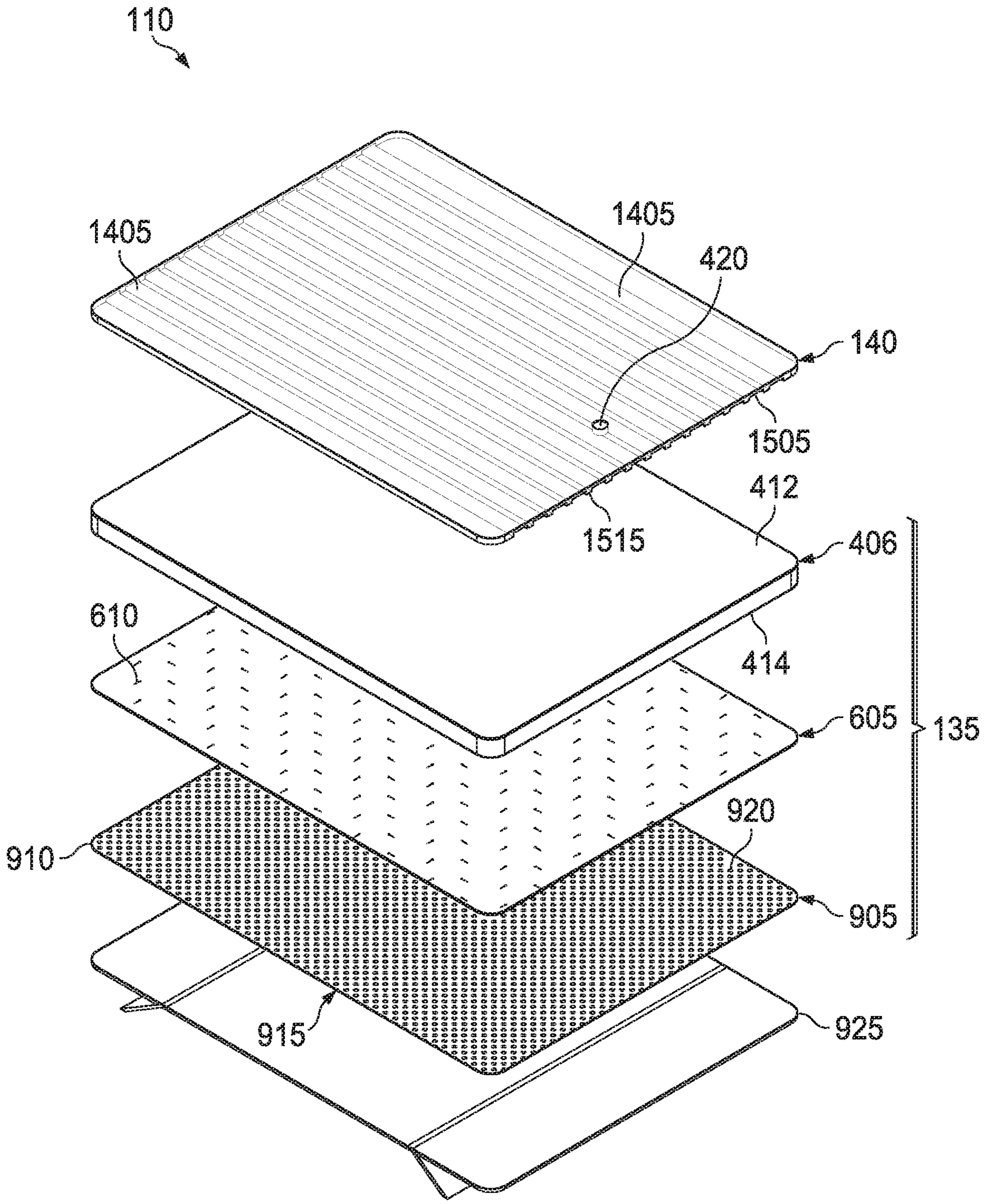
FIG. 18 is an exploded, isometric view of yet another exemplary dressing with fluid transport features.

FIG. 18 is an exploded isometric view of yet another exemplary dressing 110, illustrating additional details that may be associated with some embodiments. In some embodiments, the dressing 110 may be similar to that of FIG. 9 with fluid transport features 1405 (e.g. similar to those described above) on the cover 140. So for example, the cover 140 may have a plurality of fluid transport features 1405 on its interior surface 1505 (e.g. facing and/or contacting the second surface 412 of the manifold 406). In some embodiments, at least some of the fluid transport features 1405 may comprise capillary channels, for example with ridges 1515 contacting the second surface 412 of the manifold 406. In some embodiments, the fluid transport features 1405 may extend longitudinally and may be configured to transport liquid longitudinally along the elongate length of the dressing 110. In some embodiments, the fluid transport features 1405 may extend for approximately the length of the manifold 406.

Some dressing 110 embodiments may further comprise a fluid-control layer 605, which may comprise a substantially fluid-impermeable polymer film with a plurality of fluid passages (such as perforations 610) extending through the polymer film. In some embodiments, the first surface 414 of the manifold 406 may be disposed adjacent to the fluid-control layer 605. For example, the manifold 406 may be disposed between the cover 140 and the fluid-control layer 605. The fluid control layer 605 of FIG. 18 may be similar to that of FIG. 6. In some embodiments, the fluid passages (e.g. perforations 610) may be approximately coextensive with the first surface 414 and/or the fluid control layer 605.

Some dressing 110 embodiments may further comprise a sealing layer 905 disposed adjacent to the fluid control layer 605 opposite the manifold 406. In some embodiments, the sealing layer 905 may be similar to that of FIG. 9. In some embodiments, the sealing layer 905 may be configured to removably adhere and/or seal the dressing 110 to the tissue site. In some embodiments, the sealing layer 905 may have a plurality of apertures 920, which may be at least partially aligned with the fluid passages (e.g. perforations 610) of the fluid control layer 605. In some embodiments, each fluid passage (e.g. perforation 610) may be aligned with an aperture 920 of the sealing layer 905. In some embodiments, the sealing layer 905 may be approximately coextensive with the fluid control layer 605 and/or the manifold 406. In some embodiments, the sealing layer 905 may comprise an adhesive surface opposite the fluid-control layer 605. The adhesive surface of the sealing layer 905 may be configured to releasably attach the dressing 110 to the tissue site and/or to seal the dressing 110 to the tissue site. Some embodiments may further comprise one or more sealing layer release liners 925 contacting (e.g. spanning) the adhesive surface of the sealing layer 905.

In some embodiments, the sealing layer 905 may comprise a gel layer. For example, the sealing layer 905 may comprise a hydrophobic gel and has a hardness of approximately 5-80 Shore OO. In some embodiments, the sealing layer 905 may comprise silicone gel. In some embodiments, the silicone gel may have an area density less than 300 grams per square meter. While the cover 140 in FIG. 18 is shown as a sheet (with fluid transport features 1405 on the interior surface 1505) which is substantially coextensive with the manifold 406, in other embodiments, the cover 140 may have other shapes. For example, the cover 140 may be a sheet that is larger than the manifold 406, so that a border region, typically with the attachment device, may extend beyond the manifold 406 to envelope the manifold 406 when the dressing 110 is applied on the tissue site. In some embodiments, the cover 140 may comprise a bag-like configuration (not shown) having an open end configured to receive the manifold 406.

Figure 19:
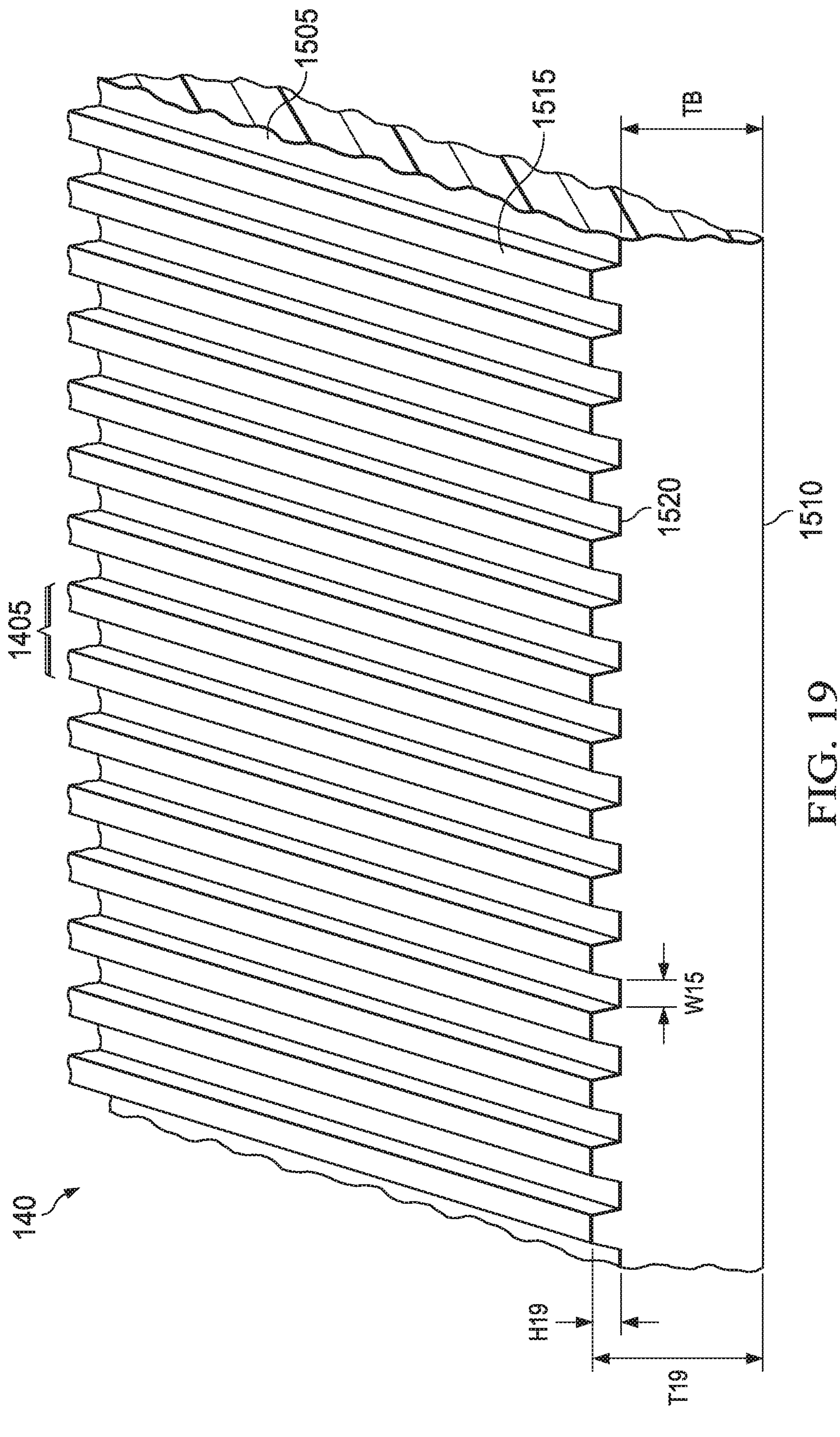
FIG. 19 is a schematic cut-away view of an exemplary cover, of the sort which might be used with the exemplary dressings of FIGS. 14-18, shown here inverted so that the interior surface of the cover with the fluid transport features is located on top for clear viewing.

FIG. 19 is a schematic cut-away view of an exemplary cover 140, of the sort which might be used with respect to FIGS. 14-18, illustrating additional details that may be associated with some embodiments. In FIG. 19, the cover 140 is shown inverted (e.g. compared to FIG. 15), so that the interior surface 1505 of the cover 140 with the fluid transport features 1405 is located on top for clear viewing. FIG. 19 better illustrates exemplary ridges 1515 and grooves 1520, which form the fluid transport features 1405 in FIG. 19. For example, each channel (e.g. fluid transport feature 1405) may be formed by a groove 1520 between two adjacent ridges 1515. In some embodiments, the ridges 1515 and grooves 1520 may all be approximately the same size. In some embodiments, the ridges 1515 and grooves 1520 may all be sized for capillary action. In some embodiments, the ridges 1515 may have a height H19 of approximately 5-3000 micron, approximately 25-3000 micron, or approximately 5-350 micron. In some embodiments, the ridges 1515 may have a width or thickness of approximately 30-250 micron. In some embodiments, the adjacent ridges 1515 may be spaced apart so that the width W15 of the grooves 1520 between the ridges 1515 is approximately 5-3000 micron, approximately 25-3000 micron, or approximately 5-350 micron. In some embodiments, the spacing of the ridges 1515 by width W15 may be approximately the same distance as the height H19 of the ridges 1515. In some embodiments, the film of the cover 140 may have a total thickness T19 of approximately 5000 micron or less. In some embodiments, the flat base of the film from which the ridges 1515 project may have a thickness TB of approximately 75 micron or less. In some embodiments, the ridges 1515 and the base from which they project may be formed of the same material, forming an integral cover 140 with ridges 1515 on the interior surface 1505 and a substantially flat exterior surface 1510. In some embodiments, the ridges 1515 and grooves 1520 may be approximately linear, all the ridges 1515 may extend approximately parallel to one another, and all of the grooves 1520 may extend approximately parallel to one another. In some embodiments, the ridges 1515 may be flat-topped. In some embodiments, the cover 140 may further comprise a hydrophobic or a hydrophilic coating on the interior surface 1505. For example, the interior surface 1505 of the channels of the cover 140 may comprise a hydrophilic surface, which may be sufficiently hydrophilic to allow liquid, such as exudate, to wet the surface of the channels. In some embodiments, only the grooves 1520 may be coated, for example with the notch between ridges 1515 and/or the walls of the ridges 1515 being coated, but the free ends of the ridges 1515 not being coated.

Figure 20:
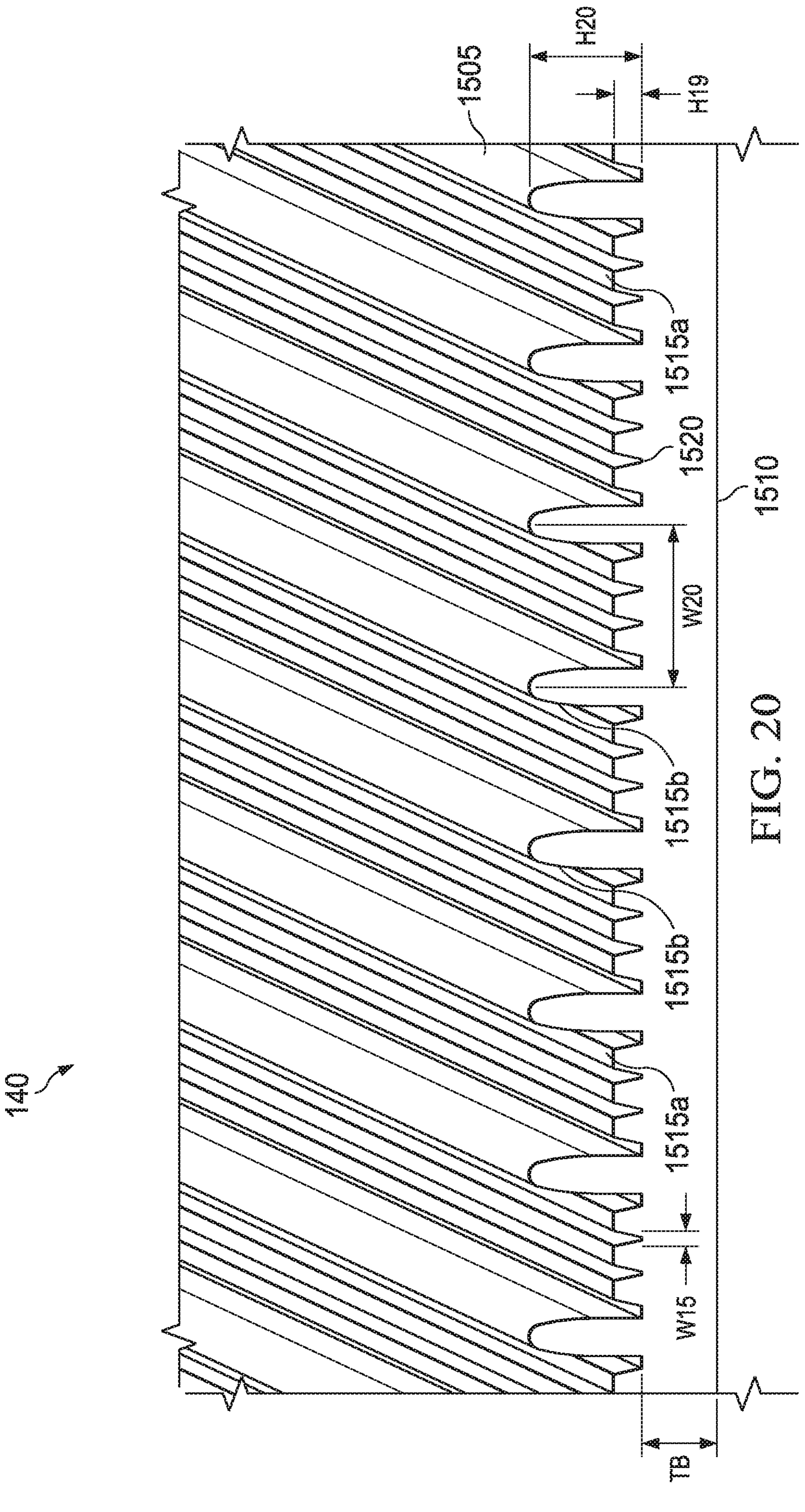
FIG. 20 is a schematic cut-away view of an alternate cover embodiment for an exemplary dressing, oriented with the interior surface and fluid transport features facing upward.

FIG. 20 is a schematic cut-away view of an alternate cover 140 embodiment for an exemplary dressing 110, illustrating additional details that may be associated with some embodiments. Similar to FIG. 19, the cover 140 of FIG. 20 is shown inverted (e.g. compared to FIG. 15), so that the interior surface 1505 of the cover 140 with the fluid transport features 1405 is located on top for clear viewing. As shown in FIG. 20, in some cover 140 embodiments, not all of the channels may be identically sized and/or shaped. In some embodiments, the channels may be configured to allow and/or provide two different mechanisms for fluid movement through the dressing 110 independent of the manifold 406 (e.g. for a total of three separate fluid transport mechanisms for the dressing 110). For example, some channels may be configured for capillary action, and some channels may be configured for fluid transport due to negative pressure differential within the dressing 110.

In some embodiments, the plurality of ridges 1515 may comprise a first portion of taller ridges 1515*b* and a second portion of shorter ridges 1515*a*, with the taller ridges 1515*b* having a height greater than the shorter ridges 1515*a*. In some embodiments, the shorter ridges 1515*a* (and the grooves 1520 therebetween) may be configured to form channels for capillary action, and the taller ridges 1515*b* (and the space between adjacent taller ridges 1515*b*) may be configured to form channels for fluid transport due to negative-pressure differential within the dressing 110 (e.g. between the cover 140 and the manifold 406). For example, the taller ridges 1515*b* may all be approximately the same height H20, the shorter ridges 1515*a* may all be approximately the same height H19, and the shorter ridges 1515*a* may have height H19 less than the height H20 of the taller ridges 1515*b*. In some embodiments, the shorter ridges 1515*a* may have height H19 of approximately 5-350 micron, and/or the taller ridges 1515*b* may have height H20 of approximately 5-3000 micron, approximately 25-3000 micron, approximately 50-3000 micron, approximately 75-1500 micron, or approximately 100-1000 micron. In some embodiments, the shorter ridges 1515*a* may have height H19 of approximately 0.5-80% of the height H20 of the taller ridges 1515*b*. In some embodiments, the shorter ridges 1515*a* may have height H19 of approximately 5-50% of the height H20 of the taller ridges 1515*b*. In some embodiments, two or more (e.g. three) of the shorter ridges 1515*a* may be located between adjacent taller ridges 1515*b*. In some embodiments, the grooves 1520 between adjacent shorter ridges 1515*a* (and/or between adjacent shorter ridges and taller ridges) may have a width W15 of approximately 5-350 micron (e.g. sized for capillary action); and/or the space/gap between adjacent taller ridges 1515*b* may have a width W20 of approximately 25-3000 micron. In some embodiments, the grooves 1520 between adjacent shorter ridges 1515*a* may have width W15 which is approximately the same size as the height H19 of the shorter ridges 1515*a*. In some embodiments, the space/gap between adjacent taller ridges 1515*b* may have width W20 which is approximately the same size as the height H20 of the taller ridges 1515*b*. In some embodiments, the ridges 1515 and grooves 1520 may be approximately linear, all the ridges 1515 may extend approximately parallel to one another, and all of the grooves 1520 may extend approximately parallel to one another. In some embodiments, the shorter ridges 1515*a* may be flat-topped. In some embodiments, the taller ridges 1515*b* may be rounded at the free end. In some embodiments, the grooves 1520 between adjacent shorter ridges 1515*a* may be v-shaped. In some embodiments, at least some of the ridges (e.g. the smaller ridges 1515*a*) may be shaped in cross-section so that the width of each such ridge at the bottom is greater than the width of the ridge at the top.

FIG. 20 illustrates the fluid transport features 1405 on the interior surface 1505 of the cover 140 for an example dressing 110 which may be configured to provide two additional fluid transport mechanisms, in addition to negative pressure distribution through the manifold 406. In some embodiments, the taller ridges 1515*b* may be configured to form flow channels for transportation of fluid via negative pressure differential; and the shorter ridges 1515*a* may be configured for capillary action (e.g. to transport fluid by capillary action). In some embodiments, the configuration with shorter ridges 1515*a* between adjacent taller ridges 1515*b* may form a plurality of capillary channels (e.g. located between adjacent shorter ridges and/or between adjacent shorter and taller ridges) and a plurality of negative-pressure fluid transport channels (e.g. located between adjacent taller ridges). For example, each of the negative-pressure fluid transport channels may be stacked atop (e.g. overlying) a plurality of smaller capillary channels, with the capillary channels (defined between the shorter ridges) located in proximity to the base of the cover 140 film and between the flat base and the negative-pressure fluid transport channels (defined between adjacent taller ridges 1515*b*). When used with a manifold in a dressing, only the taller ridges 1515*b* may contact the second surface of the manifold in some embodiments. For example, the size, spacing, shape, rigidity of the ridges 1515*b* and/or the stiffness and/or pore size of the manifold may prevent significant intrusion of the manifold between the taller ridges 1515*b* during negative-pressure therapy, and/or may prevent the manifold from contacting the shorter ridges 1515*a* and/or from intruding into the grooves 1520 between shorter ridges 1515*a*. In some embodiments, the manifold may not occlude or intrude within either the channels between the taller ridges 1515*b* or the channels between the shorter ridges 1515*a* during negative-pressure therapy. In some embodiments, the interaction of the manifold with the taller ridges 1515*b* and/or the shorter ridges 1515*a* may form enclosed capillary action channels. In some embodiments, the taller ridges 1515*b* may be configured to form larger channels configured for capillary action; and the shorter ridges 1515*a* may be configured to form smaller channels for capillary action.

In some embodiments, the cover 140 may comprise or consist essentially of a fluid control film or a fluid transport film similar to that described in U.S. Pat. No. 6,420,622, herein incorporated by reference to the extent it is not inconsistent with the explicit disclosure herein.

In some embodiments, the cover 140 may further comprise a hydrophobic or a hydrophilic coating on the interior surface 1505. For example, the interior surface 1505 of the channels of the cover 140 may comprise a hydrophilic surface, which may be sufficiently hydrophilic to allow liquid, such as exudate, to wet the surface of the channels. In some embodiments, only the grooves 1520 may be coated, for example with the notch between ridges 1515 and/or the walls of the ridges 1515 being coated, but the free ends of the ridges 1515 not being coated. In some embodiments, only the shorter ridges 1515*a* and the grooves adjacent the shorter ridges may be coated. For example, the portion of the taller ridges 1515*b* extending beyond the shorter ridges 1515*a* may not be coated.

In some example embodiments, a method for manufacturing a dressing (e.g. similar to those of FIGS. 14-20) may comprise: providing a manifold; and providing a cover having an interior surface, configured so that at least a portion of the interior surface faces towards the manifold, and a plurality of fluid transport features on at least a portion of the interior surface. In some embodiments, at least some of the plurality of fluid transport features may be configured for capillary action. For example, the plurality of fluid transport features may comprise a plurality of channels sized for capillary action. In some embodiments, the manifold may be elongate, and the plurality of channels may extend longitudinally. Some method embodiments may further comprise attaching the cover to a surface of the manifold. Some embodiments may further comprise providing an attachment device having a treatment aperture, and positioning the manifold so that at least a portion of the manifold (e.g. opposite the cover) is exposed to, faces, and/or is in fluid communication with the tissue site through the treatment aperture. Some embodiments may further comprise attaching the cover to the attachment device. In some embodiments, the cover may comprise a top cap and a plurality of sidewalls. In some embodiments, the fluid transport features may be located on the top cap and/or the sidewalls. For example, the method may comprise forming a cover with a top cap and a plurality of sidewalls. In some embodiments, forming the cover may further comprise forming the top cap to have at least some of the plurality of fluid transport features and/or forming the sidewalls to have at least some of the fluid transport features. Some embodiments may further comprise providing a fluid control layer, a comfort layer, and/or a sealing layer. Some embodiments may further comprise positioning the fluid control layer and/or the comfort layer between the manifold and the tissue site, for example between the manifold and the treatment aperture of the attachment device. In some embodiments, providing a cover may comprise providing a polymer film, for example comprising polyurethane or polyethylene, and forming the fluid transport features on the interior surface. Some embodiments may further comprise orienting the cover with respect to the elongate manifold so that the fluid transport features extend longitudinally. Some embodiments may further comprise forming a port in the cover, configured for introduction of negative pressure into the dressing. In some embodiments, the method of manufacture (for example, further describing providing the polymer film to comprise manufacturing of the film with specific features) and/or other details regarding the product or uses of the product may be similar to those described in U.S. Published Patent Appl. No. 2017/0045285, herein incorporated by reference to the extent it is not inconsistent with the explicit disclosure herein.

In some example embodiments, a method of using a dressing may comprise: applying a negative-pressure dressing (similar to disclosed embodiments as shown in FIGS. 14-20) to a tissue site, applying negative pressure to the dressing, and transporting fluid (e.g. longitudinally and/or towards a port) within the dressing via capillary action. For example, the dressing may comprise a plurality of channels (e.g. ridges and grooves) which are configured for capillary action. In some embodiments, the manifold may not effectively transport fluid under negative pressure (e.g. the manifold may be clogged), and the capillary action fluid transport may allow fluid movement despite ineffective distribution of negative pressure throughout the dressing. Some method embodiments may further comprise orienting the dressing vertically, wherein transporting fluid via capillary action may transport fluid vertically even when the negative pressure within the dressing is insufficient to effectively transport fluid vertically.

The systems, apparatuses, and methods described herein may provide significant advantages. For example, some dressing embodiments may be configured to provide negative-pressure therapy to a tissue site. Some embodiments may also be configured to drain exudate from a tissue site, for example moving exudate or other liquid through the dressing to the port (and thereby toward the negative-pressure source). In some embodiments, the dressing may be configured with multiple pathways or mechanisms for fluid transport through the dressing to the port leading to the negative-pressure source. This may enable the dressing to continue to function properly (e.g. for negative-pressure therapy and/or for exudate removal) even if the manifold of the dressing becomes clogged and/or even if the manifold is vertically oriented. For example, if the manifold becomes clogged (e.g. so that the negative-pressure differential in the manifold is insufficient to effectively transport the exudate to the port), some dressing embodiments may allow for alternate fluid transport through the dressing using larger channels (e.g. formed by taller ridges) that provide for negative-pressure fluid transport other than through the manifold. In some embodiments, if the manifold becomes clogged (e.g. so that the negative-pressure differential in the manifold is insufficient to effectively drain the exudate), the dressing may allow for fluid transport without the manifold via capillary action. In some embodiments, if fluid transport is diminished due to vertical orientation of the dressing (e.g. due to a larger fluid head), some dressing embodiments may allow for alternate fluid transport through the dressing using larger channels (e.g. formed by taller ridges) that provide for negative-pressure fluid transport other than through the manifold. In some embodiments, if fluid transport is diminished due to vertical orientation of the dressing (e.g. due to a larger fluid head), the dressing may allow for fluid transport without the manifold via capillary action.

If something is described as "exemplary" or an "example", it should be understood that refers to a non-exclusive example. The terms "about" or "approximately" or the like, when used with a number, may mean that specific number, or alternatively, a range in proximity to the specific number as understood by persons of skill in the art field (for example, +/−10%). Use of broader terms such as "comprises", "includes", and "having" should be understood to provide support for narrower terms such as "consisting of", "consisting essentially of", and "comprised substantially of". Use of the term "optionally", "may", "might", "possibly", "could", "can", "would", "should", "preferably", "typically", "often" and the like with respect to any element, component, feature, characteristic, etc. of an embodiment means that the element, component, feature, characteristic, etc. is not required, or alternatively, the element, component, feature, characteristic, etc. is required, both alternatives being within the scope of the embodiment(s). Such element, component, feature, characteristic, etc. may be optionally included in some embodiments, or it may be excluded (e.g. forming alternative embodiments, all of which are included within the scope of disclosure). Section headings used herein are provided for consistency and convenience, and shall not limit or characterize any invention(s) set out in any claims that may issue from this disclosure. If a reference numeral is used to reference a specific example of a more general term, then that reference numeral may also be used to refer to the general term (or vice versa).

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing, the container, or both may be eliminated or separated from other components for manufacture or sale. In other example configurations, the controller may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims. Also, features, elements, and aspects described with respect to a particular embodiment may be combined with features, elements, and aspects described with respect to one or more other embodiments.

What is claimed is:

1. A negative-pressure dressing for use on a tissue site, comprising:
- a manifold having a first surface and a second surface; and
- a cover configured to be disposed over the manifold, wherein the cover comprises:
  - an interior surface configured so that at least a portion of the interior surface faces towards the second surface of the manifold,
  - an exterior surface,
  - a port configured for introduction of negative pressure through the cover, and
  - a plurality of fluid transport features on at least a portion of the interior surface configured for capillary action, wherein the plurality of fluid transport features comprise a plurality of channels including a plurality of ridges and a plurality of grooves, wherein the grooves have a hydrophilic coating, and wherein a free end of the ridges do not have the hydrophilic coating.

2. The dressing of claim 1, wherein the channels have a width of approximately 5-3000 micron.

3. The dressing of claim 1, wherein the manifold is elongate; and the fluid transport features are oriented to extend longitudinally along an elongate length of the manifold.

4. The dressing of claim 1, wherein the cover further comprises a plurality of sidewalls and a cap; and the fluid transport features are located on the cap.

5. The dressing of claim 4, wherein the plurality of sidewalls of the cover comprise two longitudinal sidewalls and two end sidewalls; and the fluid transport features also are located on the longitudinal sidewalls.

6. The dressing of claim 4, wherein the fluid transport features are located on all of the sidewalls.

7. The dressing of claim 1, wherein at least some of the grooves have a width configured to provide fluid transport via capillary action, even without negative pressure.

8. The dressing of claim 1, wherein the channels are configured to provide two different mechanisms for fluid movement through the dressing independent of the manifold.

9. The dressing of claim 1, wherein the plurality of ridges comprise a first portion of taller ridges and a second portion of shorter ridges; the taller ridges have a height greater than the shorter ridges; and two or more of the shorter ridges are located between each pair of adjacent taller ridges.

10. The dressing of claim 9, wherein the taller ridges are configured to form flow channels for transportation of fluid under negative pressure; and the shorter ridges are configured to transport fluid by capillary action.

11. The dressing of claim 9, wherein the shorter ridges have a height of approximately 5-350 micron and the taller ridges have a height of approximately 25-3000 micron, wherein the groove between adjacent shorter ridges is approximately 5-350 micron, and wherein a space between adjacent taller ridges has a width of approximately 25-3000 micron.

12. The dressing of claim 1, further comprising an attachment device configured to sealingly attach the cover to the tissue site.

13. The dressing of claim 12, wherein the attachment device comprises a treatment aperture; the manifold is configured for the first surface to be at least partially facing and in fluid communication with the tissue site through the treatment aperture; and the cover is configured to be disposed over the manifold and coupled to the attachment device around the manifold.

14. The dressing of claim 12, wherein the cover further comprises a flange; and the attachment device is configured to attach the flange to the tissue site.

15. The dressing of claim 14, wherein the fluid transport features are substantially coextensive with the interior surface of the cover except for the flange.

16. The dressing of claim 1, wherein the cover contacts the second surface of the manifold.

17. The dressing of claim 1, wherein the cover is not directly attached to the second surface of the manifold.

18. The dressing of claim 1, wherein the cover further comprises a flat base from which the ridges project, and the flat base has a thickness of approximately 75 micron or less.

19. The dressing of claim 1, wherein the fluid transport features are substantially coextensive with the interior surface along a portion of the cover adjacent to the manifold.

20. The dressing of claim 1, further comprising a fluid control layer comprising a substantially fluid-impermeable polymer film with a plurality of fluid passages extending through the polymer film; wherein the first surface of the manifold is disposed adjacent to the fluid control layer.

21. The dressing of claim 20, further comprising a sealing layer disposed adjacent to the fluid control layer opposite the manifold, wherein the sealing layer has a plurality of apertures at least partially aligned with the fluid passages of the fluid control layer.

22. The dressing of claim 1, wherein the cover comprises a bag-like configuration having an open end configured to receive the manifold.

23. A negative-pressure dressing for use on a tissue site, comprising:
- an attachment device having a treatment aperture;
- a manifold having a first surface and a second surface and configured for the first surface to be at least partially exposed to the tissue site through the treatment aperture; and
- a cover configured to be disposed over the manifold and coupled to the attachment device around the manifold, wherein the cover comprises:
  - an interior surface configured with a top cap portion facing towards the second surface of the manifold,
  - an exterior surface,
  - a port configured for introduction of negative pressure through the cover, and
  - a plurality of exudate transport features on at least a portion of the interior surface configured for capillary action, wherein the plurality of exudate transport features comprise a plurality of channels including a plurality of ridges and a plurality of grooves, wherein the grooves have a hydrophilic coating, and wherein a free end of the ridges do not have the hydrophilic coating.

24. The dressing of claim 23, wherein the manifold is elongate; and the exudate transport features are oriented to extend longitudinally.

25. A negative-pressure dressing for use on a tissue site, comprising:

a fluid-control layer comprising a substantially fluid-impermeable polymer film with a plurality of fluid passages extending through the polymer film;

a manifold having a first surface, a second surface, and a thickness therebetween, wherein the first surface is disposed adjacent to the fluid-control layer; and a substantially fluid-impermeable cover configured to be disposed over the manifold, wherein the cover comprises:

an interior surface configured with at least a portion of the interior surface facing towards the second surface of the manifold, an exterior surface, a port configured for introduction of negative pressure through the cover, and a plurality of liquid channeling features on at least a portion of the interior surface which are configured for capillary action, wherein the plurality of liquid channeling features comprise a plurality of channels including a plurality of ridges and a plurality of grooves, wherein the grooves have a hydrophilic coating, and wherein a free end of the ridges do not have the hydrophilic coating.

26. The dressing of claim 25, further comprising a sealing layer disposed adjacent to the fluid control layer opposite the manifold, the sealing layer having a plurality of apertures at least partially aligned with the fluid passages of the fluid control layer.

27. The dressing of claim 26, wherein the manifold is elongate;

and the liquid channeling features are oriented to extend longitudinally.

28. An elongate negative-pressure dressing for use on a tissue site, comprising:

a manifold having a first surface configured to face the tissue site and an opposite second surface; and a cover configured to be disposed over the manifold, wherein the cover comprises:

an interior surface configured so that at least a top cap portion of the interior surface faces towards the second surface of the manifold, and a plurality of micro-molded features on at least a portion of the interior surface configured for longitudinal fluid transport along an elongate length of the dressing, wherein the plurality of micro-molded features comprise a plurality of ridges and a plurality of grooves, wherein the grooves have a hydrophilic coating, and wherein a free end of the ridges do not have the hydrophilic coating.

* * * * *